US010299944B2

(12) United States Patent
Al-Lamee et al.

(10) Patent No.: US 10,299,944 B2
(45) Date of Patent: May 28, 2019

(54) METHOD OF PRODUCING A TUBE FOR USE IN THE FORMATION OF A STENT, AND SUCH TUBE

(71) Applicant: Arterius Limited, Leeds, West Yorkshire (GB)

(72) Inventors: Kadem Al-Lamee, Leeds (GB); Adrian Kelly, Bradford (GB); Philip D. Coates, Bradford (GB); Glen P. Thompson, Bradford (GB); Phil Caton-Rose, Bradford (GB)

(73) Assignee: ARTERIUS LIMITED, Leeds (GB)

( * ) Notice: Subject to any disclaimer, the term of this patent is extended or adjusted under 35 U.S.C. 154(b) by 442 days.

(21) Appl. No.: 14/430,497

(22) PCT Filed: Sep. 24, 2013

(86) PCT No.: PCT/GB2013/052499
§ 371 (c)(1),
(2) Date: Mar. 23, 2015

(87) PCT Pub. No.: WO2014/045068
PCT Pub. Date: Mar. 27, 2014

(65) Prior Publication Data
US 2015/0230946 A1    Aug. 20, 2015

Related U.S. Application Data

(60) Provisional application No. 61/704,795, filed on Sep. 24, 2012.

(30) Foreign Application Priority Data

Sep. 24, 2012   (GB) .................................. 1217018.9

(51) Int. Cl.
*B29C 55/30*   (2006.01)
*B29C 55/24*   (2006.01)
(Continued)

(52) U.S. Cl.
CPC .................. *A61F 2/82* (2013.01); *A61F 2/04* (2013.01); *B29C 47/0023* (2013.01);
(Continued)

(58) Field of Classification Search
CPC ......... B29C 55/22; B29C 55/24; B29C 55/26; B29C 55/30; B29C 70/52–70/528;
(Continued)

(56) References Cited

U.S. PATENT DOCUMENTS 2,561,569 A  *  7/1951  Flynn ................ A61M 25/0009
                                                    264/149
3,201,827 A  *  8/1965  Reynolds ................ B29C 55/24
                                                    26/83
(Continued)

FOREIGN PATENT DOCUMENTS

CN    1228690 A    9/1999
CN    1882293 A    12/2006
(Continued)

OTHER PUBLICATIONS

Coates, P.D. et al., "Drawing of Polymers through a Conical Die," Polymer 20, Dec. 1979, 1553-1560.
(Continued)

*Primary Examiner* — Jeffrey M Wollschlager
(74) *Attorney, Agent, or Firm* — HoustonHogle LLP

(57) ABSTRACT

Bioresorbable polymeric tubes suitable for use in a stent have been produced by a using a die drawing technique, comprising: —deforming an orientable, thermoplastic polymer tubing (4) in the solid phase by drawing it over a mandrel (1) and/or through a die (3), where the mandrel (1) has a lead end and an exit end and the die (3) has an entry side and an exit side, wherein a drawing mechanism applies a drawing tension to the tubing (4) from the exit end of the mandrel (1) and/or the exit side of the die (3), said tension
(Continued)

being insufficient to cause tensile failure of the tubing but sufficient to deform the tubing, thereby drawing the tubing over the mandrel (1) and/or through the die (3) in the solid phase to induce uniaxial or biaxial orientation of the polymer; and —collecting the deformed tubing from the exit end of the mandrel (1) and/or the exit side of the die (3).

21 Claims, 7 Drawing Sheets

(51) Int. Cl.

| | | |
|---|---|---|
| *B29C 55/22* | (2006.01) | |
| *A61F 2/04* | (2013.01) | |
| *A61F 2/82* | (2013.01) | |
| *B29C 47/00* | (2006.01) | |
| *B29C 55/26* | (2006.01) | |
| *B29D 23/00* | (2006.01) | |
| *B29L 23/00* | (2006.01) | |
| *B29C 70/52* | (2006.01) | |

(52) U.S. Cl.
CPC .............. *B29C 55/26* (2013.01); *B29C 55/30* (2013.01); *A61F 2210/0004* (2013.01); *B29C 55/22* (2013.01); *B29C 55/24* (2013.01); *B29C 70/52* (2013.01); *B29D 23/00* (2013.01); *B29K 2995/006* (2013.01); *B29L 2023/007* (2013.01)

(58) Field of Classification Search
CPC .......... B29C 47/0023; A61F 2/82; A61F 2/04; A61F 2210/0004; B29L 2023/007; B29D 23/00

See application file for complete search history.

(56) References Cited

U.S. PATENT DOCUMENTS

| | | | |
|---|---|---|---|
| 4,254,072 A | 3/1981 | Capaccio et al. | |
| 4,528,832 A * | 7/1985 | Fuchs, Jr. ............ | B21C 23/005 156/244.14 |
| 4,801,419 A * | 1/1989 | Ward ................. | B29C 55/30 264/288.4 |
| 5,401,257 A * | 3/1995 | Chevalier, Jr. .... | A61M 25/0017 604/265 |
| 5,650,114 A * | 7/1997 | Ward ................. | B29C 55/30 264/290.2 |
| 5,702,656 A * | 12/1997 | Sarver ................. | B29C 31/041 264/102 |
| 5,782,906 A * | 7/1998 | Marshall ............. | A61F 2/07 623/1.15 |
| 5,817,270 A * | 10/1998 | Prenger .............. | B29C 47/0023 264/209.4 |
| 5,942,171 A * | 8/1999 | Prenger .............. | B29C 47/0023 264/209.5 |
| 5,948,332 A * | 9/1999 | Prenger .............. | B29C 47/0023 264/209.5 |
| 6,048,480 A * | 4/2000 | Doyle ................ | A61L 27/16 264/138 |
| 6,187,054 B1 * | 2/2001 | Colone .............. | A61F 2/07 128/898 |
| 6,214,283 B1 * | 4/2001 | Visscher ............. | B29C 47/0023 264/237 |
| 6,276,863 B1 * | 8/2001 | Alkelin .............. | F01D 5/025 403/273 |
| 7,226,558 B2 * | 6/2007 | Nieman .............. | A61F 2/06 264/175 |
| 7,687,002 B2 | 3/2010 | Nichols et al. | |
| 7,846,361 B2 | 12/2010 | Thatcher et al. | |
| 7,971,333 B2 | 7/2011 | Gale et al. | |
| 2002/0022101 A1 * | 2/2002 | Lenthe ................ | B29C 47/0023 428/36.9 |
| 2003/0141617 A1 * | 7/2003 | Prevotat ............. | B29C 47/0023 264/40.7 |
| 2004/0068287 A1 * | 4/2004 | Lim .................. | A61M 25/1029 606/194 |
| 2004/0148014 A1 | 7/2004 | Nuutinen et al. | |
| 2005/0137678 A1 | 6/2005 | Varma | |
| 2006/0020330 A1 | 1/2006 | Huang et al. | |
| 2006/0041102 A1 | 2/2006 | Hossainy et al. | |
| 2007/0207186 A1 * | 9/2007 | Scanlon .............. | A61F 2/07 424/424 |
| 2007/0288080 A1 * | 12/2007 | Maccollum ......... | A61F 2/82 623/1.11 |
| 2008/0054511 A1 | 3/2008 | Varma | |
| 2008/0103584 A1 | 5/2008 | Su et al. | |
| 2008/0177374 A1 | 7/2008 | Zheng et al. | |
| 2009/0105800 A1 | 4/2009 | Sabaria | |
| 2009/0228094 A1 | 9/2009 | Yan et al. | |
| 2009/0315208 A1 | 12/2009 | Headley, Jr. et al. | |
| 2009/0319028 A1 | 12/2009 | Ramzipoor et al. | |
| 2010/0025894 A1 | 2/2010 | Kleiner et al. | |
| 2010/0076556 A1 | 3/2010 | Tomantschger et al. | |
| 2010/0244334 A1 | 9/2010 | Contiliano et al. | |
| 2011/0049751 A1 | 3/2011 | Gada et al. | |
| 2011/0062638 A1 * | 3/2011 | Glauser .............. | B29C 55/26 264/532 |
| 2011/0130521 A1 | 6/2011 | Thatcher et al. | |
| 2011/0190871 A1 | 8/2011 | Trollsas et al. | |
| 2012/0029614 A1 | 2/2012 | Burnside et al. | |
| 2012/0091633 A1 | 4/2012 | Wang et al. | |
| 2012/0221097 A1 | 8/2012 | Schmid et al. | |

FOREIGN PATENT DOCUMENTS

| | | |
|---|---|---|
| CN | 101156965 A | 4/2008 |
| CN | 201551421 U | 8/2010 |
| EP | 0157601 B1 | 3/1985 |
| EP | 1908484 A2 | 4/2008 |
| GB | 2156733 A | 10/1985 |
| JP | S60-236724 | 11/1985 |
| JP | H09-241412 | 9/1997 |
| WO | 199205943 | 4/1992 |
| WO | 98/00090 | 1/1998 |
| WO | 2004023985 A2 | 3/2004 |
| WO | 2005/023149 A2 | 3/2005 |
| WO | WO 2005065582 | 7/2005 |
| WO | 2006014747 A1 | 2/2006 |
| WO | 2008154608 A1 | 12/2008 |
| WO | 2011008883 A1 | 1/2011 |
| WO | 2011031872 A2 | 3/2011 |
| WO | 2013003644 A1 | 1/2013 |

OTHER PUBLICATIONS

D'Souza, S. et al., "Biodegradable Stents—A New Era?" European Cardiology, 2008, 82-84.
GB Search Report issued in GB Application No. 1217018.9, entitled "Methods." Date of Search: Feb. 19, 2013. 2 pages.
GB Search Report issued in GB Application No. 1217018.9, entitled "Methods." Date of Search: Jul. 18, 2013. 3 pages.
Kukureka, S.N. et al., "Analysis and Modelling of the die Drawing of Polymers," Journal of Material Science 27, 1992, 3379-3388.
Morath, C.C. et al., "The Development of Continuous Large-scale Die Drawing for the Production of Oriented Polymer Rods and Tubes," Plastics, Rubber and Composites Processing and Applications 19, 1993, 55-62.
Moravej, M. et al., "Biodegradable Metals for Cardiovascular Stent Application: Interests and New Opportunities," International Journal of Molecular Sciences, 2011, 4250-4270.
Oberhauser, J., "Engineering Bioresorbable Polymers into Vascular Scaffolds—An Application in Interventional Cardiology," Abbott Laboratories, Feb. 10, 2011. 33 pages.
Onuma, Y. et al., "Bioresorbable Scaffold—The Advent of a New Era in Percutaneous Coronary and Peripheral Revascularization?" Circulation, 2011, 779-797.
Topol, E., "The Disappearing Stent: Bioabsorbable Stents." 2008: http://www.theheart.org/article/842901.do. 13 pages.

(56) References Cited

OTHER PUBLICATIONS

Ward, I.M. et al., An Introduction to the Mechanical Properties of Solid Polymers, 2nd Edition. 2004 John Wiley & Sons Ltd., Chichester, UK, 1-26.
Ward, I.M. et al., Solid Phase Processing of Polymers, 2000 Hanser Gardner Publishing, 357-361.
International Preliminary Report on Patentability, dated Apr. 2, 2015, from counterpart International Patent Application No. PCT/GB2013/052499, filed on Sep. 24, 2013.
Further Examination Report, dated Apr. 16, 2018, from New Zealand Patent Application No. 707348. 3 pages.
Notice of Reason for Rejection, dated Apr. 26, 2018, from Japanese Patent Application No. 2015-532511 filed Nov. 9, 2015. 9 pages.
International Search Report issued in International Application No. PCT/GB2013/052499, entitled "Method of Producing a Tube for Use in the Formation of a Stent, and Such Tube," Date of Search: Jan. 10, 2014.

\* cited by examiner

METHOD OF PRODUCING A TUBE FOR USE IN THE FORMATION OF A STENT, AND SUCH TUBE

This application is the U.S. National Stage of International Application No. PCT/GB2013/052499, filed Sep. 24, 2013, which designates the U.S., published in English, which claims priority to GB Application No. 1217018.9 filed Sep. 24, 2012 and claims the benefit of U.S. Provisional Application No. 61/704,795, filed Sep. 24, 2012. The entire teachings of the above applications are incorporated herein by reference.

FIELD OF THE INVENTION

The present invention relates to a tube comprising a polymeric material suitable for use as a stent, and methods for fabricating the same.

BACKGROUND

The listing or discussion of an apparently prior-published document in this specification should not necessarily be taken as an acknowledgement that the document is part of the state of the art or is common general knowledge.

There are many medical situations where it is necessary or desirable to implant a stent within a patient in order to prevent or counteract a constriction in a naturally occurring vessel or passage. In this context, a "stent" is an artificial tubular structure which is able to apply force radially outwardly on a vessel or passage of a patient in order to maintain patency of the vessel or passage and permit fluid flow through said vessel or passage.

One of the main uses of stents is in the treatment of cardiovascular disease, which is a leading cause of mortality within the developed world. Coronary disease is of most concern and patients having such disease usually have narrowing in one or more coronary arteries. One treatment is coronary stenting, which involves the placement of a stent at the site of acute artery closure. This type of procedure has proved effective in restoring vessel patency and decreasing myocardial ischemia.

Stents are also commonly used in the treatment of other conditions caused by the narrowing of the vasculature, for example, peripheral arterial disease and renal vascular hypertension.

Current stent technology is based on the use of permanent stents made from corrosion-resistant metals, such as 316L stainless steel, or metal alloys, such as cobalt chromium or nitinol. The inherent strength of metals mean that stents made from such metallic tubes can adopt a low profile while exhibiting the radial strength needed to maintain vessel patency (i.e. keeping the vessel in an open and unobstructed state) whilst retaining a low profile. The profile of a stent is to be understood as relating to its physical dimensions, in particular, its wall thickness and diameter.

However, despite their low profile and radial strength characteristics, there are a number of disadvantages associated with the use of permanent metallic implants. In particular, exposure of the currently used metallic stents to flowing blood can result in thrombus formation, smooth muscle cell proliferation and acute thrombotic occlusion of the stent. Furthermore, metallic stents have specific drawbacks which limit their widespread use throughout the body. These limitations include long-term endothelial dysfunction, delayed re-endothelialisation, thrombogenicity, permanent physical irritation, chronic inflammatory local reactions, mismatches in mechanical behaviour between stented and non-stented vessel areas, inability to adapt to growth in young patients, and importantly non-permissive or disadvantageous characteristics for later surgical revascularization.

The major effect of stent implantation is provided by its scaffolding effect, which is required to last for between 6 to 12 months, during which time vessel patency can be restored to near normal levels. After this period of time, the presence of a stent within the vessel does not usually provide any beneficial effects in the long term as regards its role as a supporting structure.

In the light of the disadvantages associated with permanent metallic stents, the general consensus amongst medical practitioners over recent years has been the desire to move away from using permanent stents and towards using non-permanent biodegradable stents.

In order for the use of biodegradable stents to be realised in a clinical setting, they must possess the following: (1) Mechanical strength—the biodegradable stent must exhibit mechanical strength approaching that of metallic stents so that it can retain a low profile while at the same time being able to withstand the radial pressures exerted upon it in the vessel environment; (2) Optimum degradation profile—the stent must remain in place and maintain its structural integrity long enough for vessel patency to be restored. However, once the task of supporting the vessel has been achieved, degradation of the stent needs to be reasonably swift so as to prevent the onset of any unwanted side-effects. It should be noted that this balancing act is not as trivial as it first appears; and (3) Biocompatibility—the degradation products of many bioabsorbable compounds are capable of eliciting inflammatory immune responses. Therefore, the materials comprising the stent and their degradation products must be biocompatible in that they do not elicit such responses.

Many biodegradable stents are undergoing development and a number of fully biodegradable stents are currently being examined in a number of clinical trials. In addition to adopting purely a support role within the vessel, many biodegradable stents are also designed to be drug eluting. Such stents have been assessed in clinical trials and include Abbot's BVS Stent (Ormiston J. A., et al. *Lancet*, 2008, 371, p 899-907) and Biotronic's Magnesium Stent (Erbel R., et al. *Lancet*, 2007, 369, p 1869-1875). By way of a specific example, Abbott's BVS stent is fabricated from a biodegradable polyester derived from lactic acid (poly-L-lactic acid, PLLA) with a coating that controls release of the drug everolimus to prevent rejection and reclogging. An example of a non drug eluting biodegradable stent is Igaki Medical's Igaki-Tamai's stent (Tamai H., et al. *Circulation*, 2000, 102, p 399-404), which is also fabricated from PLLA.

In order for stents to function effectively they must have a radial strength capable of withstanding the radial compressive forces exerted by the luminal wall of a blood vessel. Moreover, they must exhibit sufficient flexibility to allow for crimping onto a balloon catheter for the journey through the tortuous vascular network to the site of deployment and for expansion at said site of deployment.

Temporary stents have been made from biodegradable metallic tubing, for example, Biotronic's Magnesium Stent. This stent is a tubular, slotted stent sculpted by laser from a tube of a biodegradable magnesium alloy. Like the permanent stainless steel stents, it has low elastic recoil, with minimum shortening after inflation. Despite having these properties, only limited success has been observed in clinical trials. This has partly been attributed to the relatively rapid rate of degradation of 60 to 90 days.

Given the problems associated with the rapid degradation of such biodegradable metallic stents, stents made from biodegradable polymeric tubing are attractive. Firstly, a myriad of polymeric materials are already known in the art as compared to biodegradable metals, which are essentially limited to the use of magnesium and iron.

Secondly, the degradation rates of biodegradable polymers are in the range of months and years and so are generally slower than that of biodegradable metals, which are generally measured in weeks. Furthermore, it is possible to alter the degradation rate of a polymeric material to suit specific needs by adjusting the composition of the polymer or polymer blend used. However, despite these advantages, there are a number of problems that need to be overcome in order to make stents fashioned from biodegradable polymers a viable alternative to metallic stents.

The inherent properties of metals mean that they are ideal for producing low profile stents exhibiting the radial strength required to maintain the lumen of the blood vessel open. Compared to metals and metal alloys, polymers have an inferior strength to weight ratio. Therefore, if a polymeric stent is compared to a metallic stent having a similar slot/mesh size and strut/wall thickness it would be lacking in the mechanical strength required to withstand the radial forces exerted upon it by a blood vessel wall. There are various solutions to compensate for this strength differential, however none are ideal.

The radial strength of a polymeric stent can be increased by reducing the cell size of the mesh. However, the problem with decreasing the cell size is that the flexibility of the stent is reduced, which can make implantation of the stent difficult because blood vessels are not perfectly cylindrical in shape and thus the natural conformation of a blood vessel may be lost when the stent is implanted.

The radial strength can also be improved by increasing the thickness of the stent wall struts. However, this increases the profile of the stent and there is evidence that suggests that having thicker struts in a mesh stent results in a greater likelihood of restenosis after implantation of the stent.

Therefore, it would be highly desirable to produce tubing made from a biodegradable material with mechanical strength characteristics such that it could be fashioned into a stent having a similar strut and mesh size common amongst permanent metallic stents that are currently used in the clinic.

Polymeric tubing formed by extruding a polymer melt from, for example, a single or twin screw extruder, exhibits minimal alignment of the polymer molecules. Alignment of these molecules in both the radial and axial directions improves the overall properties of the tubing. A number of techniques, such as blow molding and die drawing, can deform polymeric tubing so as to induce molecular orientation of the polymer molecules, in either a uni- or biaxial fashion, thus strengthening said tubing.

In the context of polymer tubing, blow molding is a process whereby a tube, fixed at both ends by some form of grip and held within a cylindrical mould, is heated to a temperature between its glass transition and melting temperature. To achieve the target diameter gas is then pumped through the heated tubing to push the walls of the tubing against the boundary created by the mold.

Blow molding has previously been used to manufacture polymeric tubing for use in biodegradable stents. For examples of blow molding techniques, see US 2010/00258894 A1, US 2010/0198331 A1, U.S. Pat. No. 7,971, 333 B2 and US 2011/0062638 A1. Given the nature of these blow molding techniques, they are unable to produce tubing with the size required for stents in a continuous manner. Furthermore, there is a considerable amount of waste material retained in the fixing means.

Die drawing is a process whereby a polymeric material is heated to a temperature between its glass transition and melting temperature, and pulled through a die to change its cross sectional area. The deformation during this change in cross-sectional area causes orientation and alignment of the polymer molecules which gives improvements in terms of strength and stiffness. Unlike blow molding techniques, die drawing can also produce tubing in a continuous manner because the process does not require the tubing to be fixed at both ends. However, die drawing has never been used to produce tubes capable of being used for stents.

In U.S. Pat. No. 4,801,419 a die drawing process was used to produce oriented polymeric tubing. In one example, a length of unplasticised PVC thick walled tubing having an inner diameter of 32 mm and an outer diameter of 42 mm was drawn over the expanding cone of a mandrel and through a die, to give a die drawn tube with a wall thickness of 3.7 mm. Similarly, tubing having a wall thickness of 0.225 mm was produced in U.S. Pat. No. 5,650,114, by deforming a tube over an expanding former (mandrel). The resultant tubes produced by these methods are useful in the fields of gas piping etc., but are not suitable for use in the manufacture of stents due to their large size.

Die drawing is a thermal process. Therefore, scaling such processes, in particular, down-scaling, is non-trivial due to the differences in volumes, surface areas and heat transfer rates involved. The polymeric materials that are used in bioresorbable stents are highly temperature and moisture sensitive which adds to the difficulty of producing tubing suitable to use in stents by die drawing. This is in contrast to the conventional pipe grade plastic used in the above mentioned die drawing processes.

Typically, stents are manufactured from polymeric tubes by using a laser to cut away the wall of the tube to create the required mesh-like scaffolding structure of a stent. As laser cutting can be particularly sensitive to fluctuations in the thickness of the tube wall the tube must have a uniform shape and consistent wall thickness along its length for the process to be successful. While blow molding can achieve the required uniform dimensions without significant difficulties, uniformity is difficult to attain with die drawing techniques.

In view of the above, a die drawing process that consistently produces tubing having the dimensions suitable for use in a stent, i.e. a wall thickness of less than 150 microns and an outer diameter of 1-3 mm, would be useful as no such technique has been disclosed.

Therefore, to address the above-mentioned problems the present inventors have devised a die drawing method for the production of polymeric tubing for use in stents, said tubing having optimal, or otherwise improved, mechanical strength and shape characteristics.

The above discussion has focussed on tubing for use in coronary, peripheral, cardiothoracic, and neuro vascular stents but it is to be understood that the present invention is not limited thereto. Tubing for stents other than vascular stents, such as tubing for ureteral, urethral, duodenal, colonic and biliary stents are also relevant to the current invention.

SUMMARY OF INVENTION

For the avoidance of doubt, when used herein, any ranges presented are inclusive of the end-points.

According to the current invention there is provided a tube for use in a stent comprising a polymeric material having a wall thickness that is from 75 microns to 150 microns, optionally wherein the tube has a tensile modulus from 2,500 to 6,000 MPa and a tensile yield strength from 90 to 600 MPa (e.g. 90 to 300 MPa).

When used herein, the term "tube" or "tubing" relates to a hollow and substantially cylindrical object.

When used herein, the term "tensile modulus" means the ratio of the tensile stress to the tensile strain over the range for which this ratio is constant. When mentioned herein, this term can also be used interchangeably with the terms "elastic modulus", "modulus of elasticity" and "Young's modulus".

When used herein, the term "tensile yield strength" is the measure of the stress at which a material begins to deform plastically. When used herein, this term can also be used interchangeably with the term "yield strength" and "yield point".

Embodiments of the present invention include those in which the polymeric material is bioresorbable and the breakdown products are biocompatible.

When used herein, the term "bioresorbable" refers to polymers that are capable of being either completely or partially degraded and/or eroded when exposed to bodily fluids such as blood and can be gradually resorbed, adsorbed, and/or eliminated by the body. When used herein, this term can be used interchangeably with the terms "biodegradable", bioerodible", "bioabsorbable".

When used herein, the term "biocompatible" means that the polymer and polymer breakdown products are not toxic to mammalian organisms and do not cause injurious effects, such as inflammation, on biological systems.

In other embodiments, the polymeric material is oriented in the axial and radial directions of the tube.

When used herein, the term "oriented" means that there is molecular alignment of the polymer molecules.

In further embodiments of the present invention the ultimate tensile strength of the tube is from 90 to 800 MPa (e.g. from 90 MPa to 800 MPa, such as 120 MPa to 600 MPa, 150 MPa to 400 MPa, or 200 MPa to 300 MPa).

When used herein, the term "ultimate tensile strength" refers to the maximum stress a material can withstand while being stretched or pulled by an applied load.

In embodiments of the present invention the flexural strength of the tube is from 50 MPa to 1000 MPa (e.g. from 50 MPa to 500 MPa, such as 80 MPa to 400 MPa, 100 MPa to 300 MPa, or 120 MPa to 250 MPa).

When used herein, the term "flexural strength" is defined as the maximum flexural stress a material of a specific cross section is able to withstand during flexural deformation.

In embodiments of the present invention the flexural modulus of the tube is from 2000 MPa to 10000 MPa (e.g. from 2000 MPa to 8000 MPa, such as 2500 MPa to 7000 MPa, 3000 MPa to 6500 MPa, or 3500 MPa to 6000 MPa).

When used herein, the term "flexural modulus" is defines as the ratio of stress to strain under flexural deformation within its elastic limit. In other words, it is a measure of the stiffness of a material under flexural load.

In certain embodiments of the present invention the hoop yield strength of the tube is from 50 to 800 MPa (e.g. from 50 MPa to 500 MPa, such as 80 MPa to 300 MPa, 80 MPa to 160 MPa, or 100 MPa to 160 MPa).

When used herein, the term "hoop yield strength" refers to the measure of the stress at which a tubular material begins to deform plastically while being stretched or pulled by an applied load exerting a circumferential force on said material.

In further embodiments of the present invention the ultimate hoop strength of the tube is from 90 to 800 MPa (e.g. from 90 MPa to 500 MPa, such as 100 MPa to 300 MPa, 100 MPa to 180 MPa, or 110 MPa to 160 MPa).

When used herein, the term "ultimate hoop strength" refers to the maximum stress a material can withstand while being stretched or pulled by an applied load exerting a circumferential force on said material.

In another embodiment of the present invention, the tube has an inner diameter from 0.5 to 4.0 mm and an outer diameter from 0.9 mm and 15 mm, such as an inner diameter from 1.70 to 2.10 mm or from 1.2 to 1.8 mm and an outer diameter from 1.5 mm to 2.5 mm or from 2.00 to 2.30 mm.

In a yet further embodiments, the tube of the present invention has a wall thickness of 75, 100 and 150 microns.

In other embodiments, the tubing comprises polymeric material wherein the polymeric material is albumin, collagen, hyaluronic acid and derivatives thereof, sodium alginate and derivatives thereof, chitosan and derivatives thereof, gelatin, starch, cellulose polymers, casein, dextran and derivatives thereof, polysaccharides, fibrinogen, poly (valerolactone), polydioxanone, and copolymers of lactide and 1,4-dioxane-2-one, poly(hydroxybutyrate), poly(hydroxyvalerate), poly(hydroxybutyrate-co-hydroxyvalerate) copolymers, poly(alkylcarbonate), poly(orthoesters), tyrosine based polycarbonates and polyarylates, poly(ethylene terephthalate), poly(anhydrides), poly(ester-amides), polyphosphazenes, poly(amino acids), poly-L-lactic acid (PLLA), poly-D,L-lactic acid (PDLLA), polyglycolic acid (PGA), copolymers of polylactic acid, polyglycolic acid (PLGA), polycaprolactone, poly (4-hydroxybutyrate) (P4HB), polydioxanone, poly (trimethylene carbonate), poly (hydroxybutyrate-hydroxyvalerate), polyorthoester; poly (ester amides), poly (ortho esters), polyanhydrides, poly (anhydride-co-imide), poly (propylene fumarate), pseudo poly (amino acid), poly (alkyl cyanoacrylates), polyphosphazenes, and polyphosphoester, such as poly (D,L-lactide), poly(glycolide) or copolymers and/or blends thereof (e.g. Poly (L-lactide)).

In certain embodiments, the polymeric material is poly (L-lactide), poly (D,L-lactide), or poly(glycolide) or copolymers and/or blends thereof, such as poly (L-lactide).

In another embodiment, the tubing comprises a polymeric material wherein the polymeric material has a crystallinity of 5% or above, such as from 10% to 90%, from 20% to 80%, from 30% to 70%, from 40% to 60%, or from 30% to 50% (e.g. 45%).

In other embodiments, the tubing has an average molecular weight (Mw) from 10,000 to 10,000,000 g/mol, such as from 10,000 to 5,000,000 g/mol, from 40,000 to 3,000,000 g/mol, from 43,000 to 2,600,000 g/mol, from 100,000 to 1,000,000 g/mol, from 200,000 to 600,000 g/mol, from 225,000 to 500,000 g/mol, from 250,000 to 450,000 g/mol, and from 400,000 to 450,000 g/mol (e.g. 425,000 g/mol).

A further aspect of the current invention relates to a stent formed from the tubing of the present invention.

In certain embodiments the stent is used as a vascular stent, a ureteral stent, a urethral stent, a duodenal stent, a colonic stent or a biliary stent, in particular the stent is a coronary stent or a peripheral vascular stent (e.g. the stent is a coronary stent).

In another embodiment, the stent is expandable.

In embodiments of the invention the stent inner diameter is from 0.5 to 4.5 mm when expanded for coronary stents, such as or from 2.0 to 4.5 mm, or from 4.0 to 10.0 mm when expanded for peripheral vascular stents (e.g. 5.0 to 8.0 mm).

In other embodiments, the stent biodegrades over a period of 6 months to 36 months following implantation in an organism (e.g. 8 months to 18 months, such as 10 months to 12 months).

In further embodiments, the stent is capable of withstanding expansion pressures of from 5 to 20 bar (e.g. 7 to 15 bar, such as 10 to 12 bar).

In yet further embodiments of the invention, the stent comprises radioopaque markers selected from one or more of platinum, tantalum, tungsten, barium carbonate, bismuth oxide, barium sulfate, metrazimide, iopamidol, iohexol, iopromide, iobitridol, iomeprol, iopentol, ioversol, ioxilan, iodixanol, iotrolan, acetrizoic acid derivatives, diatrizoic acid derivatives, iothalamic acid derivatives, ioxithalamic acid derivatives, metrizoic acid derivatives, iodo theophylline derivatives, iodo-dipyridamol derivatives, iodo mopdamol derivatives, iodamide, lyophylic agents, iodipamide and ioglycamic acid or, by the addition of microspheres or bubbles which present an acoustic interface.

In yet a further embodiment, the stent further comprises a biologically active agent.

When used herein, the term "biologically active agent" includes chemical and natural substances which exert a beneficial effect on living organisms. When used herein, this term can be used interchangeably with the term "pharmaceutically active agent".

In embodiments of the current invention, the biologically active agent is selected from one or more agents selected from anti-proliferatives, anticoagulants, coronary vasodilators, anti-inflammatories, cytotoxic agents, antibiotics and radioactive agents or targets thereof, for local radiation therapy.

When used herein, the term "antiproliferative agent" includes agents that inhibit cellular proliferation in the body.

When used herein, the term "coronary vasodilator" includes agents that cause dilation of the coronary blood vessels, and hence alleviate the symptoms of reduced coronary blood flow associated with coronary artery disease.

In other embodiments, the stent further comprises an acid scavenging agent.

When used herein, the term "an acid scavenging agent" includes agents which can function in the body to neutralise acidic degradation products of the polymers that comprise the stent.

In a preferred embodiment, the acid scavenging agents are theophylline, dipyridamole, mopidamol or derivatives or iodo-derivative of those compounds thereof. Mopidamol (and derivatives having the same pyrimido-pyrimidine structure) has both an acid scavenging effect and an anti-proliferative effect.

According to the present invention there is provided a method of producing a tube for use in the formation of a stent, said method comprising:
  deforming an orientable, thermoplastic polymer tubing in the solid phase by drawing it over a mandrel, where the mandrel has lead and exit ends, and/or through a die, where the die has an entry side and an exit side, wherein:
  a drawing mechanism applies a drawing tension to the tubing from the exit end of the mandrel, and/or the exit side of the die, said tension being insufficient to cause tensile failure of the tubing but sufficient to deform the tubing, thereby drawing the tubing over the mandrel and/or through the die in the solid phase to induce uniaxial or biaxial orientation of the polymer; and
  collecting the deformed tubing from the exit end of the mandrel and/or the exit side of the die.

When used herein, the term "thermoplastic" refers to a polymer that becomes pliable or moldable above a specific temperature (e.g. its glass melting temperature), and returns to a solid state upon cooling below that specific temperature.

In certain embodiments, the molecular weight (Mw) of the orientable, thermoplastic polymer tubing is from 10,000 to 10,000,000 g/mol, such as from 10,000 to 5,000,000 g/mol, from 40,000 to 3,000,000 g/mol, from 43,000 to 2,600,000 g/mol, from 100,000 to 1,000,000 g/mol, from 200,000 to 600,000 g/mol, from 225,000 to 500,000 g/mol, from 250,000 to 450,000 g/mol, and from 400,000 to 450,000 g/mol (e.g. 425,000 g/mol).

In other embodiments of the invention the orientable, thermoplastic polymer tubing is at a temperature above the glass transition temperature ($T_g$) and below the melting temperature ($T_m$) of the thermoplastic polymer when used in the method disclosed herein.

When used herein the term "glass transition temperature" refers to the temperature at which a polymer transitions from its hard state into a pliable or rubber-like state.

When used herein the term "melting temperature" refers to the temperature at which the polymer liquefies to a molten state.

Alternatively or additionally, when used herein, $T_m$ is the crystalline melting point of the polymer, which is the temperature at which crystals melt and a crystalline polymer resembles an amorphous polymer, which has no short-range order.

In further embodiments, the orientable, thermoplastic polymer tubing is at a temperature from 40° C. to 150° C., such as from 60° C. to 120° C., from 70° C. to 100° C., or from 75° C. to 95° C. (e.g. 85° C. or 90° C.).

In other embodiments the resultant wall thickness of the tube is from 75 to 150 microns, such as from 90 to 110 microns (e.g. 100 microns), or from 110 to 150 microns. In other embodiments, the resultant wall thickness is from 75 to 300 microns.

In embodiments of the present invention the bulk cross-sectional area of the polymeric tubing is reduced by drawing the polymeric tubing over the mandrel and/or through the die.

When used herein, the term "bulk cross-sectional area" means the area of the bulk of the tubing substantially normal to its longitudinal axis.

Further embodiments include a method wherein the orientable, thermoplastic polymer tubing is essentially unoriented before deformation.

In yet further embodiments of the present invention, the orientable, thermoplastic polymer tubing used in the method has a tag portion and the drawing mechanism comprises a haul-off comprising a gripping mechanism in which the tag portion is gripped.

In an embodiment of the invention the thermoplastic polymer tubing is extruded from a polymer melt.

In another embodiment, the orientable, thermoplastic polymer tubing used in the method of the present invention has an inner diameter from 0.5 to 4.0 mm, and an outer diameter from 0.9 mm to 15 mm, such as an inner diameter from 1.0 to 1.8 mm (e.g. 1.2 mm) and an outer diameter from 1.5 mm to 3.0 mm (e.g. 2.4 mm).

In a further embodiment, the orientable, thermoplastic polymer tubing used in the method of the present invention has a wall thickness from 0.1 mm to 4.5 mm, such as from 0.1 mm to 1.0 mm, from 0.2 mm to 0.8 mm, from 0.3 mm to 0.8 mm or from 0.4 to 0.8 mm.

In another embodiment, the orientable, thermoplastic polymer tubing is bioresorbable.

In other embodiments, the thermoplastic polymer tubing comprises polymeric material wherein the polymeric material is albumin, collagen, hyaluronic acid and derivatives thereof, sodium alginate and derivatives thereof, chitosan and derivatives thereof, gelatin, starch, cellulose polymers, casein, dextran and derivatives thereof, polysaccharides, fibrinogen, poly(valerolactone), polydioxanone, and copolymers of lactide and 1,4-dioxane-2-one, poly(hydroxybutyrate), poly(hydroxyvalerate), poly(hydroxybutyrate-co-hydroxyvalerate) copolymers, poly(alkylcarbonate), poly (orthoesters), tyrosine based polycarbonates and polyarylates, poly(ethylene terephthalate), poly(anhydrides), poly(ester-amides), polyphosphazenes, poly(amino acids), poly-L-lactic acid (PLLA), poly-D,L-lactic acid (PDLLA), polyglycolic acid (PGA), copolymers of polylactic acid, polyglycolic acid (PLGA), polycaprolactone, poly (4-hydroxybutyrate) (P4HB), polydioxanone, poly (trimethylene carbonate), poly (hydroxybutyrate-hydroxyvalerate), polyorthoester; poly(ester amides), poly (ortho esters), polyanhydrides, poly (anhydride-co-imide), poly (propylene fumarate), pseudo poly (amino acid), poly (alkyl cyanoacrylates), polyphosphazenes, and polyphosphoester, such as poly (D,L-lactide), poly(glycolide) or copolymers and/or blends thereof (e.g. Poly (L-lactide)).

In a further embodiment the thermoplastic polymer is poly (L-lactide), poly (D,L-lactide), or poly(glycolide) or copolymers and/or blends thereof, such as poly (L-lactide).

In another embodiment the diameter of the mandrel at its widest point can be from 0.01 mm to 15 mm, such as from 0.1 mm to 10 mm, from 1 mm to 5 mm, or from 2 mm to 3 mm (e.g. 2.2 mm).

In other embodiments, the diameter of the mandrel at its widest point can be from 0.01 mm to 15 mm, such as from 0.1 mm to 10 mm, from 1 mm to 5 mm, from 1 mm to 4 mm, from 1.50 mm to 3.00 mm, from 1.80 mm to 2.60 mm (e.g. 1.84 mm or 1.85 mm), or from 2.00 mm to 2.60 mm (e.g. 2.01 mm, 2.18 mm or 2.20 mm).

When used herein, the term "mandrel" is to be construed as being interchangeable with the term "mandrel head".

In other embodiments, the lead (front) end of the mandrel is tapered and/or the exit (trailing) end of the mandrel is tapered.

In a yet further embodiment the angle of inclination of the taper of the lead and/or exit end of the mandrel is from 5 to 60 degrees, such as from 10 to 30 degrees, and from 10 to 20 degrees (e.g. 15 degrees).

When used herein the term "angle of inclination" is with respect to the longitudinal axis of the mandrel. It therefore refers to the angle between the plane of the mandrel outer surface and longitudinal axis of the mandrel.

In certain embodiments, the mandrel is a cone expanding mandrel.

In further embodiments the angle of inclination of the taper of the cone is 5 to 60 degrees, such as from 10 to 30 degrees, and from 10 to 20 degrees (e.g. 15 degrees).

In certain embodiments, the mandrel is attached to a supporting means.

When used herein, the term "supporting means" refers to any device that can retain the mandrel in an axial position. Such devices can be a mandrel shaft or a restraint cable.

When used in the context of the mandrel, the term "cross-sectional area" relates to the cross sectional area at the widest point of the mandrel.

When used herein, the term "internal cross-sectional area" is the cross sectional area of the tube's hollow core, which is delineated by the internal wall of the tube.

In embodiments of the present invention the entry side of the die has a diameter from 0.4 to 8.0 mm (e.g. 0.8 to 6.0 mm, such as 1.5 to 3.5 mm) and/or the exit side of the die has a diameter from 0.8 to 15 mm (e.g. 1.0 to 10.0 mm, such as 2.0 to 5.0 mm).

In other embodiments of the present invention the die is selected from: a conical die; a converging (reducing) die; a diverging (expanding) die; and a parallel (sizing) die (e.g. a conical die).

When used herein, the term "converging" means that the die causes a reduction in the outer diameter of the tubing drawn through the die. The term can therefore be used interchangeably with "reducing".

When used herein, the term "diverging" means that the die causes an increase in the outer diameter of the tubing drawn through the die when used in conjugation with a suitable mandrel. The term can therefore be used interchangeably with "expanding".

In certain embodiments, the die semi-angle is from 0 to 50 degrees, such as from 20 to 40 degrees, and from 25 to 35 degrees (e.g. 30 degrees).

When used herein, the term "semi-angle" refers to the die semi-angle and is the angle between the vertical axis of the die and the inner wall of the die.

In certain embodiments, the ratio of the die semi-angle and the angle of inclination of the mandrel taper is in the range from 1:1 to 10:1 (e.g. from 1:1 to 5:1, such as from 1:1 to 3:1, e.g. 1:1)

In certain embodiments, the mandrel and/or the die is/are maintained at a temperature between the glass transition temperature and the melting temperature of the polymer used in the orientable, thermoplastic polymer tubing.

In further embodiments, the mandrel and/or the die is/are maintained at a temperature from 10° C. to 150° C., such as from 40° C. to 150° C., 60° C. to 120° C., from 70° C. to 100° C., or from 75° C. to 95° C. (e.g. 85° C. or 90° C.).

In certain embodiments, the draw speed is from 0.00001 to 15000 mm min$^{-1}$, such as from 0.01 to 15000 mm min$^{-1}$, from 1 to 15000 mm min$^{-1}$, from 10 to 10000 mm min$^{-1}$, from 500 to 10000 mm min$^{-1}$, or from 700 to 9000 mm min$^{-1}$.

In other embodiments, the draw speed is from 0.00001 to 15000 mm min$^{-1}$, such as from 0.01 to 15000 mm min$^{-1}$, from 1 to 15000 mm min$^{-1}$, from 10 to 10000 mm min$^{-1}$, from 10 to 1000 mm min$^{-1}$, from 10 to 500 mm min$^{-1}$, from 50 to 500 mm min$^{-1}$, from 100 to 500 mm min$^{-1}$, or from 100 to 300 mm min$^{-1}$, such as 100, 200 or 300 mm min$^{-1}$.

In certain embodiments the inner hoop draw ratio of the drawn tubing is at least 1.5.

In certain other embodiments the inner hoop draw ratio of the drawn tubing is at least 1.2.

When used herein, the term "inner hoop draw ratio" is the ratio of the inner diameter of the output tubing to the inner diameter of the input tubing.

In certain embodiments the axial draw ratio is from 1.5:1 to 15:1, such as from 2:1 to 10:1 or from 2.5:1 to 4:1.

When used herein, the term "axial draw ratio" is an indication as to the degree of elongation the tubing has undergone during the drawing process.

In certain embodiments the ratio of the axial draw ratio to the inner hoop draw ratio is in the range of 0.5:1 to 10:1 (e.g. from 0.75:1 to 5:1, such as from 1:1 to 2:1).

In certain embodiments, the method of the present invention includes a further step comprising extruding the thermoplastic polymeric tubing from an upstream extruder (e.g. a single or twin screw extruder) prior to the deformation step, optionally further comprising cooling the extruded tubing.

In further embodiments of the invention, the inner diameter of the extruded tubing is from 0.5 to 4.0 mm, such as from 1.0 mm to 3.0 mm, from 1.0 mm to 2.0 mm, from 1.0 mm to 1.8 mm, or from 1.1 mm to 1.3 mm (e.g. 1.2 mm), and the outer diameter of the extruded tubing is from 0.9 mm and 15 mm, such as from 0.9 mm to 8.0 mm, from 1.5 mm to 5.0 mm, from 1.5 mm to 3.0 mm or from 2.2 mm to 2.8 mm (e.g. 2.4 mm).

In certain embodiments, the method includes a further step comprising pre-heating the thermostatic polymer tubing to a temperature between the glass transition temperature and melting temperature of the polymer, wherein the tubing is maintained at said temperature for 1 to 60 minutes prior to deformation, such as for 2 to 10 minutes.

In further embodiments, the thermoplastic polymer tubing is pre-heated prior to deformation to a temperature from 40° C. to 150° C., such as from 60° C. to 120° C., from 70° C. to 100° C., or from 75° C. to 95° C. (e.g. 85° C. or 90° C.).

In certain embodiments the cooling of the orientable, thermoplastic polymer tubing starts while in contact with the die and/or mandrel or immediately after said tubing has been drawn over the mandrel and/or through the die.

In certain embodiments, the method comprises the use of a mandrel.

In certain embodiments, the method comprises the use of a die.

In certain embodiments, the method comprises the use of both a die and a mandrel.

In certain embodiments, the method is continuous.

In certain embodiments, the draw temperature is from 40° C. to 150° C., such as from 60° C. to 120° C., from 70° C. to 100° C., or from 75° C. to 95° C. (e.g. 85° C. or 90° C.).

When used herein, the term "draw temperature" refers to the temperature of the polymer during the die drawing process.

In certain embodiments, the method further comprises preparing a stent from a tubing subjected to the processes of said method of the present invention.

Another aspect is a tube produced by the method of the present invention.

DETAILED DESCRIPTION

Figure 1:
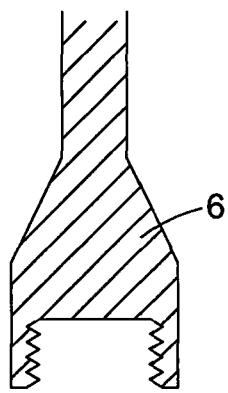
FIG. 1: A schematic diagram showing a cross-sectional view of die drawing apparatus of a first embodiment.
Figure 1:
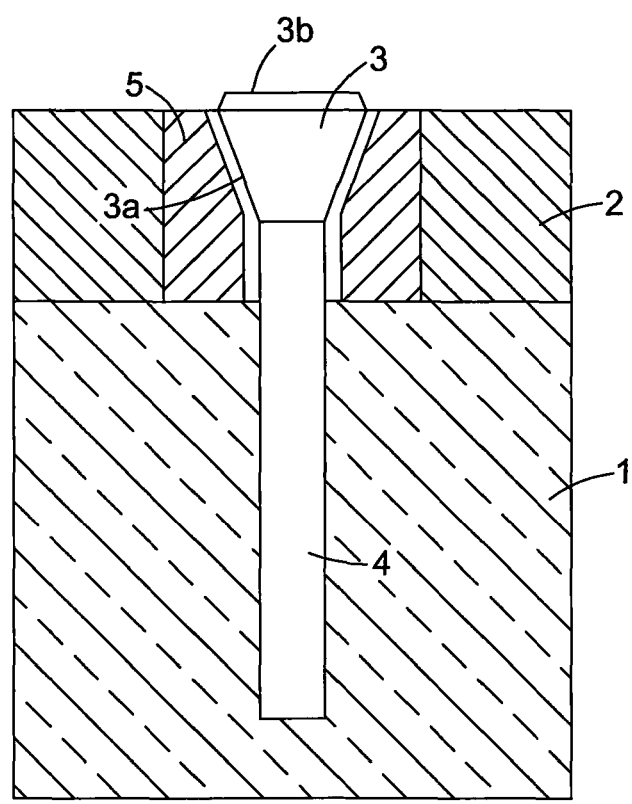

In one embodiment, the polymeric tube of the present invention has a wall thickness of 150 microns or less which is in the range typically used for metallic stents. Preferably the wall thickness is from 75 microns to 150 microns, more preferably from 90 microns to 110 microns, and most preferably the tubing has a wall thickness of approximately 100 microns.

In preferred embodiments, the polymeric tube has a tensile modulus from 2,500 to 6,000 MPa, more preferably from 3,000 to 6,000 MPa, and most preferably from 4000 to 5500 MPa. The tensile modulus can be measured by any known method, such as ASTM D638, which is the standard test method for tensile properties of rigid plastic materials. The tensile modulus is measured at 23±2° C. and at 50±5% humidity.

In other preferred embodiments, the polymeric tube has a tensile yield strength from 90 to 600 MPa (e.g. 90 to 300 MPa), and more preferably from 120 to 250 MPa. In certain other preferred embodiments, the polymeric tube has a tensile yield strength from 90 to 150 MPa, and more preferably from 110 to 130 MPa. The yield strength can be measured by any known method, such as ASTM D638, which is the standard test method for tensile properties of rigid plastic materials. The yield strength is measured at 23±2° C. and at 50±5% humidity.

The polymeric tube of the present invention has an inner diameter of from 0.5 to 4.0 mm, preferably from 1.0 mm to 1.5 mm or from 1.20 mm to 1.80 mm or from 1.70 mm to 2.10 mm, and an outer diameter of from 0.9 mm to 15 mm, preferably from 1.5 mm to 3.5 mm, more preferably from 1.5 mm to 2.5 mm, and even more preferably from 2.00 mm to 2.30 mm. Tube dimensions can be measured by any know method. For example, the outer diameter can be measured using a micrometer and the inner diameter can be measured using pin gauges. The concentricity and wall thickness of the tubing can be verified using known methods, such as by using a high resolution flat-bed scanner.

In embodiments of the present invention, the tubing has an ultimate tensile strength from 90 MPa to 800 MPa (e.g. from 120 MPa to 600 MPa). Preferably, the ultimate tensile strength is from 120 MPa to 400 MPa, or more preferably from 150 MPa to 400 MPa (e.g. from 120 MPa to 200 MPa or from 200 MPa to 300 MPa). In the context of the present invention "ultimate tensile strength" is the measure of the ability of the polymer tubing to withstand tensile stresses. The ultimate tensile strength can be measured by any known method, such as ASTM D638, which is the standard test method for tensile properties of rigid plastic materials. The ultimate tensile strength is measured at 23±2° C. and at 50±5% humidity.

In embodiments of the present invention the flexural strength of the tube may be from 50 MPa to 1000 MPa, preferably from 50 MPa to 500 MPa, more preferably from 80 MPa to 400 MPa, more preferably from 100 MPa to 300 MPa, and most preferably from 120 MPa to 250 MPa. The flexural strength is measured at 23±2° C. and at 50±5% humidity.

In embodiments of the present invention the flexural modulus of the tube may be from 2000 MPa to 10000 MPa, preferably from 2000 MPa to 8000 MPa, more preferably from 2500 MPa to 7000 MPa, more preferably from 3000 MPa to 6500 MPa, and most preferably from 3500 MPa to 6000 MPa). The flexural modulus is measured at 23±2° C. and at 50±5% humidity.

In certain embodiments of the present invention, the tubing may have a hoop yield strength from 50 MPa to 800 MPa, preferably from 50 MPa to 500 MPa, more preferably from 80 MPa to 300 MPa, more preferably from 80 MPa to 160 MPa. Most preferably, the hoop yield strength is from 100 MPa to 160 MPa. The hoop yield strength is measured at 23±2° C. and at 50±5% humidity.

In other embodiments of the present invention, the tubing may have an ultimate hoop strength of from 90 to 800 MPa, preferably from 90 MPa to 500 MPa, more preferably from 100 MPa to 300 MPa, more preferably from 100 MPa to 160 MPa. Most preferably, the ultimate hoop strength is from 110 MPa to 160 MPa. The ultimate hoop strength is measured at 23±2° C. and at 50±5% humidity.

The hoop yield strength and ultimate hoop strength can be measured, for example, by the method described in US 2010/0025894 A1.

In an embodiment, the tube of the present invention is bioresorbable and the breakdown products thereof are biocompatible. Examples of polymers that are used for the tubing of the present invention are naturally derived polymers or synthetic biodegradable polymers and copolymers. The biodegradable polymers are hydrolytically degradable polymers or enzymatically degradable polymers.

Representative examples of naturally derived polymers include albumin, collagen, hyaluronic acid and derivatives, sodium alginate and derivatives, chitosan and derivatives gelatin, starch, cellulose polymers (e.g., methylcellulose, hydroxypropyl cellulose, hydroxypropylmethylcellulose, carboxymethylcellulose, cellulose acetate phthalate, cellulose acetate succinate, hydroxypropylmethylcellulose phthalate), casein, dextran and derivatives, polysaccharides, and fibrinogen.

The synthetic biodegradable polymers and copolymers are formed from one or more cyclic monomers (e.g. D-lactide, L-lactide, D,L-lactide, meso-lactide, glycolide, [epsilon]-caprolactone, trimethylene carbonate (TMC), p-dioxanone (e.g., 1,4-dioxane-2-one or 1,5-dioxepan-2-one), or a morpholinedione). In certain embodiments, the tubing includes polymer fibers that comprise a plurality of glycolide and lactide (e.g., L-lactide, D-lactide, or mixtures thereof, also referred to as D,L-lactide) residues or meso-lactide). The ratio of glycolide to lactide residues in the copolymer is varied depending on the desired properties of the fiber. For example, the polymer has a molar ratio of glycolide residues that is greater than about 80; or greater than about 85; or greater than about 90; or greater than about 95. The fiber is formed from a polymer having a 3:97 molar ratio of lactide (e.g., D,L-lactide) to glycolide, or a 5:95 molar ratio of lactide to glycolide, or a 10:90 molar ratio of lactide to glycolide.

Other suitable polymers include copolymers prepared from caprolactone and/or lactide and/or glycolide and/or polyethylene glycol (e.g., copolymers of [epsilon]-caprolactone and lactide and copolymers of glycolide and [epsilon]-caprolactone), poly(valerolactone), polydioxanone, and copolymers of lactide and 1,4-dioxane-2-one. Other examples of biodegradable materials include poly(hydroxybutyrate), poly(hydroxyvalerate), poly(hydroxybutyrate-co-hydroxyvalerate) copolymers, poly(alkylcarbonate), poly (orthoesters), tyrosine based polycarbonates and polyarylates, poly(ethylene terephthalate), poly(anhydrides), poly(ester-amides), polyphosphazenes, or poly (amino acids).

The following hydrolytically degradable polymers are particularly preferred in the preparation of the stent: polylactic acid including poly-L-lactic acid (PLLA) and poly-D,L-lactic acid (PDLLA), polyglycolic acid (PGA), and copolymers of polylactic acid, polyglycolic acid (PLGA); polycaprolactone (PCL), poly (4-hydroxybutyrate) (P4HB); polydioxanone; poly (trimethylene carbonate); poly (hydroxybutyrate-hydroxyvalerate); polyorthoester; poly(ester amides); poly (ortho esters); polyanhydrides; poly (anhydride-co-imide); poly (propylene fumarate); pseudo poly (amino acid); poly (alkyl cyanoacrylates); polyphosphazenes; polyphosphoester. Many of these materials are discussed in Nair et al (2007) Progress in Polymer Science 32, 762-798, including the structure of the polymers and how they can be sourced or prepared.

Preferably the tubing comprises poly-L-lactic acid (PLLA) and poly-D,L-lactic acid (PDLLA), polyglycolic acid (PGA), or copolymers and/or blends thereof. More preferably, the tubing comprises a commercially available (from Purac, www.purac.com) grade of PLLA, such as Purasorb™ PL18, Purasorb™ PL24, Purasorb™ P32, Purasorb™ PL38, Purasorb™ PL49, and Purasorb™ PL65. Even more preferably, the tubing comprises Purasorb™ PL38. PL38 is an extrusion grade of semi-crystalline PLLA and this grade of polymer is used in the art to produce medical grade tubing.

Biodegradable additives are included in such polymer tubing to aid their eventual formation into stents; for example, poly(ethylene glycol) (PEG, MW 2000) can be used as a plasticizer to increase the flexibility and reduce brittle mechanical nature of PLGA.

The biodegradable tubing can comprise more than one biodegradable material. For example, a stent has a backbone of one type of material, e.g. PLLA, coated with another biodegradable material, e.g. PDLLA; the stent has a multi-layered matrix, e.g. a PLLA/PLGA structure. The material can also be a blend of more than one polymer, for example, a blend of PLLA and P4HB, or a blend of PLLA and PCL.

As mentioned above, PLGA is a L-lactide/glycolide copolymer. Various different ratios of L-lactide to glycolide monomer can be prepared as PLGA. Preferably the ratio is 85/15 L-lactide/glycolide. The preparation of PLGA and PLLA is well known in the art and many routine laboratory protocols are known such that the skilled person could readily prepare PLGA or PLLA at different molecular weights without any inventive input. Moreover PLGA and PLLA biodegradable polymers materials can be obtained commercially and FDA approved from, for example, Purac (www.purac.com) as product reference Purasorb™ PLG 8523 and Purasorb™ PL 38, respectively.

In preferred embodiments of the present invention the polymeric material is oriented in both the axial and radial directions of the tube. In alternative embodiments, the polymer is aligned in just one of the axial or radial directions of the tube. The amount of molecular alignment/orientation can be measured using any known method. For example, see the methods of measurement described in Ward I. M., et al.

J. Polym. Sci. Pol. Sym., 1977, 58, p 1-21 and Van Horn B. L., et al. Macromolecules, 2003, 36, p 8513-8521.

The crystallinity of the polymer tubing may be from 5% to 90%, preferably from 20% to 80%, more preferably from 30% to 70%, even more preferably from 40% to 60%, most preferably from 40% to 50% (e.g. 45%). The crystallinity of the tubing may be measured by any suitable method known in the art, such as differential scanning calorimetry (DSC).

In a preferred embodiment, the tube of the present invention has an outer diameter from 1.80 mm to 2.30 mm, an inner diameter from 1.70 mm to 2.10 mm, and wall thickness from 0.10 mm to 0.15 mm.

In embodiments of the present invention, a stent is prepared from the tubing of the present invention. Any known method can be used to prepare the stent, such as laser cutting or chemical etching. Preferably the stent is prepared by laser cutting the tubing to produce a mesh or slotted tube stent, preferably a mesh stent. The resultant cut stent can have any pattern known in the art. Preferably the pattern is any one of those disclosed in FIGS. 1 to 10 and the attendant description of PCT/GB2012/050882 or within the scope of Claim 1 of PCT/GB2012/050882. By stent we include a generally tubular medical device which is implantable into a lumen in the human body. A stent is generally used to prevent, or counteract, a disease-induced, localized flow constriction in the lumen. A stent prepared from the tubing of the present invention is preferably for use in a vascular lumen, for example a blood vessel. Preferably the stent is a coronary stent or a peripheral vascular stent.

In certain embodiments, the stent is either self-expandable or preferably balloon-expandable. The stent should be able expand at, and also be capable of withstanding pressures of from 5 to 20 bar, preferably pressures of from 6 to 16 bar.

When intended for use in a coronary artery, the inner diameter of the expanded stent is from 0.8 to 4.5 mm and when intended for use in a peripheral artery, the inner diameter of the expanded stent is from 2.0 to 10.0 mm.

In other embodiments of the invention, the stent made from the polymeric tubing further comprises one or more pharmaceutically active agents. These agents can be coated on the surface of the stent or they are incorporated, i.e. dissolved in the polymer or distributed in the polymer matrix either homogeneously or heterogeneously, into the polymeric material comprising the stent. In the latter example, the agent will be introduced into the human body as the stent biodegrades.

By "dissolved in the polymer" we mean that a formulation of the biodegradable material and the agent is heated so that the agent is miscible with and homogeneously mixed and dissolved in the biodegradable material.

Examples of such pharmaceutical agents include the following classes of drugs: anti-proliferatives, such as immunosuppressants (e.g. rapamycin), anti-cancer agents (e.g. paclitaxol), growth factor antagonists, migration inhibitors, somatostatin analogues, ACE-inhibitors, and lipid-lowering drugs; anticoagulants, such as direct anti-coagulants which inhibit the clotting cascade, indirect anti-coagulants, which depress the synthesis of clotting factors, antiplatelet (aggregation) drugs, such as thromboxane A2 inhibitors or antagonists, adenosine inhibitors, glycoprotein receptor IIb/IIIa antagonists, thrombin inhibitors; vasodilators, including vasoconstriction antagonists, such as ACE inhibitors, angiotensin II receptor antagonists, serotonin receptor antagonists, and thromboxane A2 synthetase inhibitors, and other vasodilators; anti-inflammatories; cytotoxic agents, such as anti-neoplastic agents, alkylating agents, anti-metabolites, mitotic inhibitors, and antibiotic antineoplastic agents; and radioactive agents or targets thereof, for local radiation therapy.

The stent can also comprise radioopaque markers, echogenic materials and/or magnetic resonance imaging (MRI) responsive materials (i.e., MRI contrast agents) to aid in visualization of the device under ultrasound, fluoroscopy and/or MRI. For example, the stent can be made with a biodegradable polymer blend containing radiopaque material therewithin or coated with a composition which is echogenic or radiopaque, e.g., made with echogenic or radiopaque with materials such as powdered tantalum, tungsten, barium carbonate, bismuth oxide, barium sulfate, metrazimide, iopamidol, iohexol, iopromide, iobitridol, iomeprol, iopentol, ioversol, ioxilan, iodixanol, iotrolan, acetrizoic acid derivatives, diatrizoic acid derivatives, iothalamic acid derivatives, ioxithalamic acid derivatives, metrizoic acid derivatives, iodamide, lypophylic agents, iodipamide and ioglycamic acid or, by the addition of microspheres or bubbles which present an acoustic interface. Visualization of a device by ultrasonic imaging is achieved using an echogenic coating. Echogenic coatings are well known in the art. For visualization under MRI, contrast agents (e.g., gadolinium (III) chelates or iron oxide compounds) are incorporated into or onto the device, such as, for example, as a component in a coating or within the void volume of the device (e.g., within a lumen, reservoir, or within the structural material used to form the device), in some embodiments, a medical device includes radio-opaque or MRI visible markers (e.g., bands) that are used to orient and guide the device during the implantation procedure. In another embodiment, these agents can be contained within the same coating layer as the compound or they are contained in a coating layer (as described above) that is either applied before or after the layer containing the combination of compounds.

In another embodiment, the stent contains an acid scavenging agent within the structure of the stent or be coated with the same. By an "acid scavenging agent" we include agents that function in the body to neutralise the acidic degradation products of the polymeric stent disclosed herein.

Many compounds having this effect are known and can be used as an acid scavenging agent. The following are examples of such agents. Pyrimido-pyrimidine compounds and its derivatives such as, for example, dipyridamole (2,6-bis(dithioethanolamino)-4,8-dipiperidinopyrimido(5,4-d)pyrimidine) and mopidamol (2,2',2'',2'''-((4-(1-piperidinyl)pyrimido(5,4-d)pyrimidine-2,6-diyl)dinitrilo)tetrakisethanol), and derivatives or dipyridamole and mopidamol having the same pyrimido-pyrimidine structure. Pyrimido-pyrimidine compounds also include VK 744 and VK 774 as described in J Clin Pathol (1972) vol. 25, 427-432. Pyrimido-pyrimidine derivatives include pyrimido [5,4-d]pyrimidine, tetrachloro (2,4,6,8-tetrachloropyrimido [5,4-d]pyrimidine (available from Bepharm Ltd (www.bepharm.com)). Also RA25, which has the same substituents in all positions of the pyrimido ring of the nitrogens of the pyrimido pyrimidine ring. Further suitable agents include those pyrimido-pyrimidine compounds, and derivatives, disclosed in Schenone et al (2008) Current Drug Therapy vol. 3, 158-176; Walland, (1979) Pharmaceutisch Weekblad, 913-917; and U.S. Pat. No. 7,799,772.

Additional acid scavenging agents include coronary vasodilator or antiproliferative agents containing tertiary amino groups; bronchodilators containing amino groups, such as theophylline and its derivatives.

Dipyridamole (Persantine) and mopidamol are well known compounds readily available commercially or using standard synthesis techniques. Preferably the acid scavenging agent is dipyridamole and/or mopidamol.

In other aspects, a stent made from the tubing of the present invention is implanted into a human or animal subject suffering from a disease, such as cardiovascular disease, for the purpose of treating said disease.

In another aspect, the present invention relates to a method of manufacturing a polymeric tubing for use in a stent. The method comprises deforming an orientable, thermoplastic polymer tubing in the solid phase by drawing it over a mandrel, where the mandrel has a lead and exit ends, and/or through a die, where the die has an entry side and an exit side, wherein a drawing mechanism applies a drawing tension to the tubing from the exit end of the mandrel and/or the exit side of the die, said tension being insufficient to cause tensile failure of the tubing but sufficient to deform the tubing, thereby drawing the tubing over the mandrel and/or through the die in the solid phase to induce uniaxial or biaxial orientation of the polymer; and collecting the deformed tubing from the exit end of the mandrel and/or the exit side of the die.

In some embodiments of the method, the orientable thermoplastic polymer is extruded polymeric tubing. The process of extruding a polymeric material to form an extruded tube is well known to those skilled in the art, and while any method of extrusion can be used, single or twin screw extrusion methods are preferred. Typically, the polymer undergoes extrusion in the molten state.

The extruded polymeric tubing is essentially unoriented before deformation. The term "essentially unoriented" when used herein means that the polymeric molecules within the extruded polymeric tubing have incurred no orientation other than that amount which results from the extrusion process.

In certain embodiments of the invention, the orientable, thermoplastic polymer tubing may have an average molecular weight from 10,000 to 10,000,000 g/mol, preferably from 10,000 to 5,000,000 g/mol, more preferably from 40,000 to 3,000,000 g/mol, more preferably from 43,000 to 2,600,000 g/mol, more preferably from 100,000 to 1,000,000 g/mol, more preferably from 200,000 to 600,000 g/mol, more preferably from 250,000 to 450,000 g/mol, even more preferably from 400,000 to 450,000 g/mol, and most preferably, approximately 425,000 g/mol.

In embodiments of the invention, the orientable, thermoplastic polymer tubing used in the method of the present invention may have: an inner diameter from 0.5 mm to 4.0 mm, preferably from 1.0 mm to 3.0 mm, more preferably 1.0 mm to 2.0 mm, more preferably from 1.0 mm to 1.8 mm, and most preferably from 1.1 mm to 1.3 mm (e.g. 1.2 mm); and an outer diameter from 0.9 mm and 15 mm, preferably from 0.9 mm to 8.0 mm, more preferably from 1.5 mm to 5.0 mm, even more preferably from 1.5 mm to 3.0 mm and most preferably from 2.2 mm to 2.8 mm (e.g. 2.4 mm).

In certain preferred embodiments, the orientable, thermoplastic polymer tubing used in the method of the present invention may have an inner diameter from 1.1 to 1.3 mm (e.g. 1.2 mm) and an outer diameter from 2.2 mm to 2.8 mm (e.g. 2.4 mm).

In other embodiments, the orientable, thermoplastic polymer tubing used in the method of the present invention may have a wall thickness from 0.1 mm to 4.5 mm, such as from 0.1 mm to 1.0 mm such as from 0.2 mm to 0.8 mm, from 0.3 mm to 0.8 mm or from 0.4 mm to 0.8 mm (e.g. 0.6 mm).

In embodiments of the method wherein the drawing apparatus comprises a mandrel, the mandrel may be any known in the art. In some embodiments, the diameter of the mandrel at its widest point may be from 0.01 to 15 mm, and preferably from 1.5 to 4.0 mm. In other embodiments, the diameter may be from 0.01 mm to 15 mm, preferably from 1.50 mm to 3.00 mm, more preferably from 1.80 mm to 2.60 mm, and even more preferably from 2.00 mm to 2.60 mm.

In embodiments of the present invention where a die is used, the mandrel is coaxially located within the die and during the normal drawing process the mandrel self-centres within the die. The position of the mandrel within the drawing apparatus may be adjustable in the axial direction. In some embodiments, the mandrel is positioned so that the apical end or lead end (depending on whether the mandrel is an expanding cone or not) resides outside the die cavity and upstream of the die entry aperture. When used herein the term "apical end" refers to the section of the mandrel proximal to the apex of the cone. In other embodiments, the mandrel is positioned so that the basal end or exit end of the mandrel resides outside the die cavity and downstream of the die exit aperture. When used herein the term "basal end" refers to the section of the mandrel proximal to the base of the cone. In yet other embodiments, the mandrel entirely resides within the cavity of the die. The position of the mandrel within the die may be selected by the user. The position of the mandrel relative to the die may be varied by routine experimentation to achieve a desired tube geometry.

The mandrel may be attached to a supporting means, examples of which include a mandrel shaft or a restraint cable. In preferred embodiments, when the apparatus is in the operating mode (i.e. a tube is being drawn), the supporting means is such that it may restrain the mandrel in the axial direction.

In certain preferred embodiments the mandrel has a lead (front) end and an exit (trailing) end (see FIG. 1). Preferably the lead end of the mandrel and/or the exit end of the mandrel is tapered. The angle of inclination of the taper is from 5 to 60 degrees, preferably from 7 to 40 degrees, most preferably from 10 to 40 degrees.

Figure 2A:
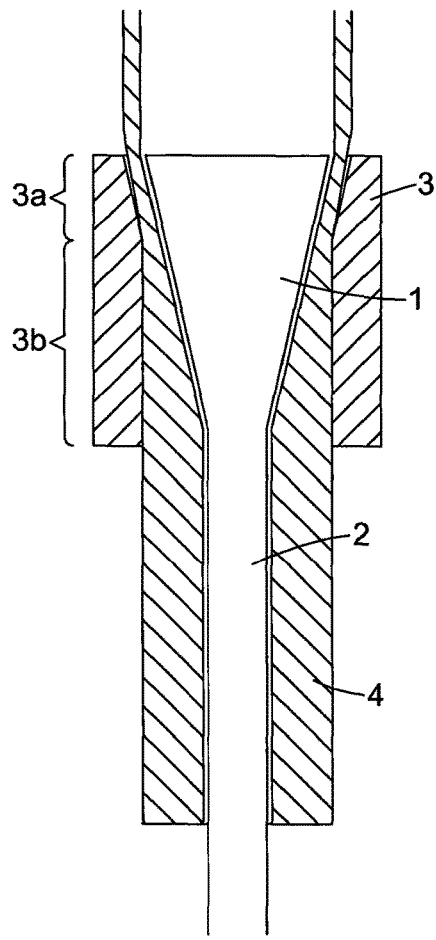
FIG. 2a: A schematic diagram showing a cross-sectional view of die drawing apparatus of a second embodiment.
Figure 2B:
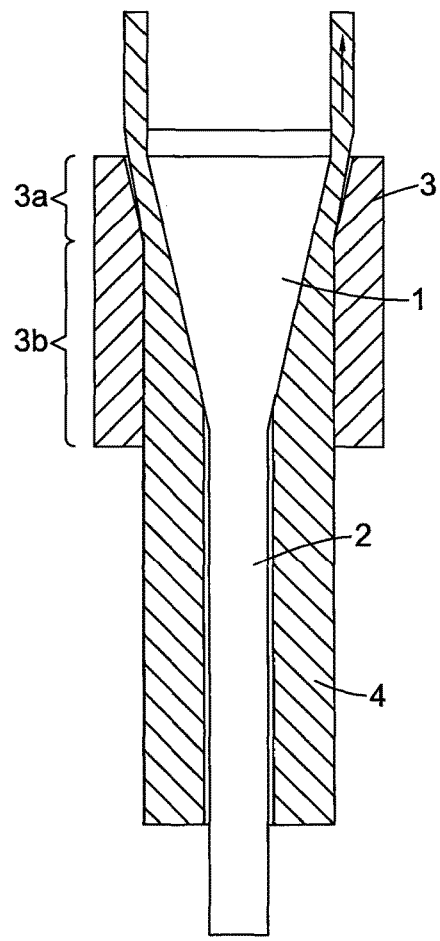
FIG. 2b: A schematic diagram showing a cross-sectional view of die drawing apparatus of an alternative arrangement of the second embodiment.

In other preferred embodiments, the mandrel is a cone expanding mandrel i.e. it is a conical mandrel (see FIGS. 2a and 2b). The conical mandrel has an apical end and a basal end. The angle of inclination of the taper of the cone may be from 5 to 60 degrees, preferably from 7 to 40 degrees, most preferably from 10 to 40 degrees.

In embodiments of the method wherein the drawing apparatus comprises a die, the die may be any die known in the art, such as a flat die or a conical die.

In embodiments of the present invention, the die has an entry side and an exit side wherein the diameter of the entry side is from 0.4 to 8.0 mm, preferably from 2.0 to 4.0 mm, and/or the diameter of the exit side is from 0.8 to 15 mm, preferably from 2.0 to 6 mm.

In certain preferred embodiments, the die is a conical die. By conical die, it is meant that the die comprises a conical cavity and the walls of said cavity are tapered. The conical die may have a semi-angle from 0 to 50 degrees, preferably from 5 to 40 degrees, most preferably from 10 to 40 degrees.

In embodiments of the invention wherein the apparatus further comprises a mandrel, a conical die is also preferred. The conical die may be a converging (reducing) die or alternatively, the conical die may be a diverging (expanding) die. In preferred embodiments, the conical die is a diverging die.

In embodiments of the present invention wherein the die is diverging, the diameter of the diameter of the entry side is from 0.4 to 8.0 mm, preferably from 2.0 to 4.0 mm, more preferably from 2.0 to 3.0 mm, even and most preferably from 2.5 to 3.0 mm.

In further embodiments of the present invention wherein the die is diverging, it is most suitable to use an expanding conical mandrel.

Preferably, the ratio of the die semi-angle and the angle of inclination of the mandrel taper is in the range from 1:1 to 10:1 (e.g. from 1:1 to 5:1). More preferably the ratio is approximately 1:1.

In a preferred embodiment of the present invention, the unoriented tubing is drawn over a mandrel having, at its widest point, a cross-sectional area at least that of the internal cross-sectional area of the tube. Therefore, the tube is fed over the mandrel (and the mandrel supporting means if present) prior to initiating the process. To achieve this, the end of the tube has a tag, preferably a belled tag. The tag is produced by heating a section of tubing above the glass transition temperature. Air or a gas (e.g. an inert gas) is then blown down the hollow of the tube to form an expanded section. After cooling, the tube is then cut across the expanded section to reveal a belled tag portion.

In embodiments where there is both a die and a mandrel, the tag portion of the tube can be fed over the mandrel so as to protrude through the exit side of the die and secured to a tensioning means applied from the exit side of the die. In other embodiments when no die is present, the tube only needs to advance to position where it is secured to the tensioning means.

With regard to the tensioning means, a suitable arrangement includes a hauloff comprising a pair of serrated jaws in which the tag is gripped and; a high tensile cable, one end of which cable is attached to the jaws, the other to a winch or a loading station to which a turning moment or mass is applied, thereby applying a axial tensile force, otherwise known as the draw tension, to the tag. Alternatively, instead of a cable, the hauloff comprises any tension transmitting means used in the drawing art including a chain, a rack and pinion mechanism, a screw mechanism and a hydraulically operated draw mechanism. The hauloff optionally further comprises a pair of continuous contra-rotating friction belts, generally known as a "Caterpillar™".

The draw tension should be sufficient to draw the tube through the die but insufficient to cause tensile failure of the tube. That is, the draw tension should be such that the true stress at any point of the product does not exceed its fracture stress at that point.

In embodiments of the method of the present invention speed at which the tubing is drawn by the tensioning means is from 0.00001 to 15000 mm min$^{-1}$, preferably from 0.01 to 15000 mm min$^{-1}$, more preferably from 1 to 15000 mm min$^{-1}$, more preferably from 10 to 10000 mm min$^{-1}$, even more preferably from 500 to 10000 mm min$^{-1}$, or most preferably from 700 to 9000 mm min$^{-1}$.

In other embodiments of the method of the present invention, the speed at which the tubing is drawn by the tensioning means is from 0.00001 to 15000 mm min$^{-1}$, preferably from 0.01 to 15000 mm min$^{-1}$, more preferably from 1 to 15000 mm min$^{-1}$, more preferably from 10 to 10000 mm min$^{-1}$, more preferably from 10 to 1000 mm min$^{-1}$, more preferably from 10 to 500 mm min$^{-1}$, even more preferably from 50 to 500 mm min$^{-1}$, yet more preferably from 100 to 500 mm min$^{-1}$, or most preferably from 100 to 300 mm min$^{-1}$ (such as 100, 200 or 300 mm min$^{-1}$).

In certain embodiments of the method of the current invention, it is desirable to soak the extruded tubing at a temperature between its glass transition temperature and its melting temperature prior to drawing over the mandrel and/or through the die. When used herein, the term "soaking" refers to exposing a tube to an above ambient temperature for a period of time that results in an increase in temperature of the tube. The soaking ensures that the tubing is at the required deformation temperature. The deformation temperature refers to the temperature of the tube at which it is to be deformed. Preferably the deformation temperature is from 2 to 50° C. below the melting temperature of the tube to be deformed. The glass transition temperature and melting temperature of homo- and copolymers will be familiar to one skilled in the art.

In other preferred embodiments, the deformation temperature is from 40° C. to 150° C., more preferably from 60° C. to 120° C., more preferably from 70° C. to 100° C., or most preferably from 75° C. to 95° C. (e.g. 85° C. or 90° C.).

In certain embodiments, the draw temperature may be from 40° C. to 150° C., preferably from 60° C. to 120° C., more preferably from 70° C. to 100° C., or even more preferably from 75° C. to 95° C. In embodiments of the invention wherein the orientable thermoplastic polymer comprises poly-L-lactic acid, the draw temperature is preferably from 75° C. to 95° C., more preferably from 80° C. to 90° C., even more preferably from 82° C. to 88° C., and even more preferably from 84° C. to 86° C. (e.g. 85° C.).

With regard to the soak time, a suitable time is from 1 minute to 60 minutes, preferably from 2 to 10 minutes. As will be appreciated by the skilled person, it is not necessary to include a soak time in all embodiments of the invention. That is, the soak time can be 0 minutes.

In other embodiments, the temperature of the process is further controlled by utilising a heated mandrel and/or a heated die, these being heated to the required deformation temperature of the tube.

In preferred embodiments the temperature of the drawing apparatus is controlled to an accuracy of ±1° C., such as with a thermostat.

Once the tubing has undergone deformation, in certain embodiments of the present invention, it is desirable to cool the drawn tubing to prevent further deformation occurring. Typically, the cooling of the tubing begins while in contact with the die and/or mandrel (i.e. when these components are not heated) or immediately after said tubing has been drawn over the mandrel and/or die if these components are heated.

It is desirable to cool tubing produced in a non-continuous batch process under tension. The cooling may be active or passive. When used herein, the term "active cooling" refers to cooling the tube through exposure of the tube to conditions below ambient temperature, e.g. by using a cooling means such as an air cooling ring located downstream from the die. When used herein, the term "passive cooling" refers to cooling the tube by allowing it to equilibrate with the ambient temperature. Die drawn tubing produced by a continuous process may be cooled actively or passively by any known method.

The bulk cross-sectional area of the polymeric tubing is reduced by drawing the polymeric tubing over the mandrel and/or through the die.

The crystallinity of the drawn tubing may be 5% or above, preferably from 5% to 90%, more preferably from 20% to 80%, even more preferably from 30% to 70%, and most preferably from 40% to 60% (such as from 40% to 50%, e.g. 45%).

Die drawn tubing produced by the method disclosed herein has greater percentage crystallinity than that of conventionally extruded tubing. While not wishing to be bound by theory, the stent produced from the die-drawn tubing of the current invention will biodegrade by a surface erosion process, rather than the bulk erosion process typically encountered in polymeric stents. For tubes and stents made according to the process of the current invention, degradation only occurs at the surface and approaches the interior in a predictable way. In contrast, bulk degradation occurs in an uncontrolled manner and this type degradation can elicit inflammatory responses in the tissues surrounding the implant site.

In another embodiment, the inner hoop draw ratio of the drawn tubing may be at least 1.5, and preferably from 1.5 to 10.0 (e.g. from 1.5 to 8.0).

In another further embodiment, the inner hoop draw ratio of the drawn tubing may be at least 1.2, preferably from 1.2 to 10.0, more preferably from 1.2 to 8.0, more preferably from 1.2 to 5.0, more preferably from 1.2 to 3.0, and most preferably from 1.2 to 2.0.

In further embodiments, the axial draw ratio may be from 1.5:1 and 15:1 (e.g. from 1.5 to 10:1, such as from 2:1 to 7:1), and preferably the axial draw ratio from 2.5:1 to 4:1.

In yet further embodiments, the ratio of the axial draw ratio to the inner hoop draw ratio may be in the range of 0.5:1 to 10:1 (e.g. 0.5:1 to 6:1, such as 0.5:1 to 2:1). The geometry of the mandrel, the die, and the tubing influences the balance of the compressive (radial) and tensile (axial) forces exerted on the tubing during the drawing process. Therefore, the ratio of the axial draw ratio and inner hoop (radial) draw ratio can be readily altered by routine experiment by varying the: geometry of the mandrel and/or die and/or extruded tubing; and/or drawing temperature; and/or drawing speed.

In other embodiments method of the current invention is continuous. Typically the hauloff comprises a pair of continuous contra-rotating friction belts although other similar devices can be envisaged. To achieve a continuous process, an extruder is set up in line with the drawing apparatus. In some embodiments, freshly extruded tube, preferably between its glass transition and melting temperature, exits an extruder barrel and is fed directly into the die drawing apparatus. In other embodiments, tubing produced by the extruder is cooled (e.g. by a cooling bath) before being fed into a reheating chamber, with said chamber heating the extruded tubing to a temperature between the glass transition and melting temperature of the polymer material. This heated tubing is then fed into the die drawing apparatus. In further embodiments where the extruder is not present, the extruded tubing is supplied to the drawing apparatus in other ways, e.g. from a motorised spool.

In a preferred embodiment of the method of the present invention, the orientable thermoplastic tubing used in the method has an inner diameter from 1.0 mm to 1.5 mm and an outer diameter from 2.0 mm to 3.0 mm; the draw temperature is from 70° C. to 100° C.; the draw speed is from 100 to 300 mm min$^{-1}$ and the mandrel diameter is from 1.80 mm to 2.40 mm. In this preferred embodiment, the angle of inclination of the mandrel taper and the die semi angle may each be independently from 15 to 50 degrees.

In a more preferred embodiment of the method, the orientable thermoplastic tubing used in the method has an inner diameter from 1.1 mm to 1.3 mm (e.g. 1.2 mm) and an outer diameter from 2.2 mm to 2.8 mm (e.g. 2.4 mm); the draw temperature is from 80° C. to 90° C. (e.g. 85° C.); the draw speed is from 100 to 300 mm min$^{-1}$ and the mandrel diameter is from 1.80 mm to 2.40 mm. In this more preferred embodiment, the angle of inclination of the mandrel taper and the die semi angle may each be independently from 20 to 40 degrees (e.g. 30 degrees) and/or the ratio of the die semi angle and the angle of inclination of the mandrel taper may be 1:1. Preferably, the die entry diameter is from 2.0 mm to 8.0 mm, more preferably from 2.0 mm to 6.0 mm, more preferably from 2.0 mm to 4.0 mm and even more preferably from 2.0 mm to 3.0 mm.

In a further preferred embodiment of the method: the orientable thermoplastic tubing used in the method has an inner diameter from 1.1 mm to 1.3 mm, an outer diameter from 2.2 mm to 2.8 mm and a wall thickness from 0.50 to 0.60 mm (e.g. 0.55 to 0.60 mm); the draw temperature is from 80° C. to 90° C.; the draw speed is from 100 to 300 mm min$^{-1}$; the mandrel diameter is from 1.80 mm to 2.40 mm; the die entry diameter is from 2.50 mm to 3.00 mm. In this further preferred embodiment the angle of inclination of the mandrel taper and the die semi angle may each be independently from 20 to 40 degrees, and/or the ratio of the die semi angle and the angle of inclination of the mandrel taper may be 1:1.

In certain preferred embodiments, the tubing produced by the method of the present invention has an outer diameter from 1.80 mm to 2.30 mm, an inner diameter from 1.70 mm to 2.10 mm, and a wall thickness from 0.10 mm to 0.15 mm.

In further embodiments of the present invention, a stent is prepared from the tubing produced by the method of the current invention. Any known method can be used to prepare the stent, such as laser cutting or chemical etching. Preferably the stent is prepared by laser cutting. By stent we include a generally tubular medical device which is implantable into a lumen in the human body. A stent is generally used to prevent, or counteract, a disease-induced, localized flow constriction in the lumen. A stent prepared from the tubing of the present invention is preferably for use in a vascular lumen, for example a blood vessel. Preferably the stent is a coronary stent or a peripheral, cardiothoracic and neuro vascular stent.

Depicted in FIG. 1 is an apparatus suitable for carrying out the method of the present invention. The apparatus comprises a first heating zone (1), a second heating zone (2), a mandrel (3) a mandrel shaft (4), a die (5), and a hauloff device (6). The die (4) is housed within the second heating zone (2) and the mandrel shaft is housed within the first (1) and second (2) heating zones.

The second heating zone (2) is located on top of the first heating zone (1) and is housed partially therewithin. However, in another embodiment, the second heating zone may be located above the first heating zone so that it sits directly thereupon. In further embodiments, there may be just a single heating zone. The heating zone(s) may each independently be heated to a temperature from 40° C. to 150° C., more preferably from 60° C. to 120° C., more preferably from 70° C. to 100° C., or most preferably from 75° C. to 95° C. (e.g. 85° C. or 90° C.). In yet further embodiments, no heating zone may be present.

As shown in FIG. 1, the mandrel (3) is connected to mandrel shaft (4) at an end that is proximal to the die (5). The base of the mandrel shaft may be anchored to the base of a tensioning means (not shown). The mandrel (3) has a tapered lead (front) and exit end (trailing) edges (3a and 3b, respectively). The angle of inclination of the taper may be from 5 and 60 degrees, preferably from 10 to 40 degrees, and more preferably from 10 to 20 degrees.

The conical die (5) depicted in FIG. 1 is a diverging (expanding) die. That is, the diameter of the die exit is greater than that of the die entry. The die entry diameter may be from 0.4 to 8.0 mm and the die exit diameter may be from 1.0 to 15 mm. The semi-angle of the die may be from 0 to 50 degrees, preferably from 10 to 40 degrees, and more preferably from 10 to 20 degrees. Alternatively, the die can be a converging (reducing) die (not shown). That is, the diameter of the die entry is greater than that of the die exit. In this alternative embodiment, the die exit diameter may be from 0.4 to 8.0 mm, preferably from and the die entry diameter may be from 1.0 to 15 mm. The semi-angle of the die may be from 0 to 50 degrees, preferably from 10 to 40 degrees, and more preferably from 10 to 20 degrees.

The mandrel (3) is fitted so that it is coaxially within the die. The mandrel can be adjusted in its axial direction in order to change the position of the mandrel head within the die. For example, in another embodiment, the mandrel can be fitted within the die so that the exit edge thereof protrudes through and out of the exit side of the die. In use, however, it is preferable that the mandrel is fixed so that it is unable to move in the axial direction. The diameter of the mandrel at its widest point may be from 0.01 mm to 15 mm, and preferably from 1.5 mm to 4.0 mm. Alternatively, the diameter may be from 0.01 mm to 15 mm, preferably from 1.50 mm to 3.00 mm, more preferably from 1.80 mm to 2.60 mm, and even more preferably from 2.00 mm to 2.60 mm.

The hauloff device (6) is positioned downstream from the die. The hauloff device may be any device mentioned herewithin or any alternative method known to the skilled person in this field.

In a typical method utilising the apparatus shown in FIG. 1, a polymeric tubing having a belled tag is fed over the mandrel shaft and mandrel head and the belled tag gripped in the jaws of the hauloff device (6). To begin the drawing process, the tensioning means (not shown) applies a force to move the hauloff device axially away from the die exit, slowly at first such that the plastic strain of the polymer tubing is increased without causing tensile failure. The draw speed is then gradually increased until a steady drawing speed is established. A suitable draw tension is determined by routine experiment by varying the draw speed of the tensioning means. In relation to draw speed, this may be from 0.00001 to 15000 mm min$^{-1}$, preferably from 0.01 to 15000 mm min$^{-1}$, more preferably from 1 to 15000 mm min$^{-1}$, more preferably from 10 to 10000 mm min$^{-1}$, even more preferably from 500 to 10000 mm min$^{-1}$, or most preferably from 700 to 9000 mm min$^{-1}$. Alternatively, the draw speed may be from 0.00001 to 15000 mm min$^{-1}$, preferably from 0.01 to 15000 mm min$^{-1}$, more preferably from 1 to 15000 mm min$^{-1}$, more preferably 10 to 10000 mm min$^{-1}$, more preferably 10 to 1000 mm min$^{-1}$, even more preferably from 10 to 500 mm min$^{-1}$, even more preferably from 50 to 500 mm min$^{-1}$, even more preferably from 100 to 500 mm min$^{-1}$, or most preferably from 100 to 300 mm min$^{-1}$. In the very most preferred embodiments the draw speed may be 100, 200 or 300 mm min$^{-1}$. Once the tube has exited the die it may be cooled as previously mentioned.

FIG. 2a shows a second embodiment of a mandrel and die arrangement suitable for carrying out the method of the present invention. As FIG. 2a focuses on an alternative die and mandrel configuration, the first and second heating zones, and hauloff device depicted in FIG. 1 have been omitted to ensure clarity.

The apparatus as depicted in FIG. 2a comprises a mandrel (1), a mandrel shaft (2), and a die (3). An alternative arrangement of this embodiment is shown in FIG. 2b. The mandrel head (1) is conically expanded. The taper of the cone as depicted in FIG. 2a is approximately 13 degrees although it may be from 5 to 60 degrees, preferably from 10 to 40 degrees, and more preferably from 10 to 30 degrees.

The mandrel head resides in whole or in part within the cavity formed by the walls of the die (2). The mandrel head is supported by a mandrel shaft (2) which serves to restrain and position the mandrel in the axial direction. The mandrel shaft may be detachable from the mandrel head. The mandrel head (1) is positioned so that it is coaxially within the die (3).

As shown, the die (3) is a conical die with a semi-angle complementary to the angle of taper of the conically expanded mandrel head i.e. the ratio of the die semi-angle and the angle of inclination of the mandrel taper is approximately 1:1. In other embodiments, the ratio of the die semi-angle and the angle of inclination of the mandrel taper may be from 1:1 to 5:1 (e.g. from 1:1 to 3:1). The die (3) as depicted in FIG. 2a is a diverging (expanding) die. That is, the die exit diameter is greater than the die entry diameter. The die entry diameter may be from 0.4 to 8.0 mm and the die exit diameter may be from 1.0 to 15 mm. In other embodiments the die may be a converging (reducing) die.

In FIG. 2a, the die (3) has an upper and lower region. The upper region (3a) is proximal to the die exit and is conical in shape, hence the die is a conical die. The lower region (3b) is proximal to the die entry and is cylindrical in shape. In other words, the semi-angle of the lower region of the die is effectively 0 degrees. In other similar embodiments the upper region of the die may be cylindrical in shape and the lower region may be conical.

FIG. 2a also shows a length of tubing (4) being drawn through the apparatus. The extruded tube may be loaded onto the mandrel as previously described. The tubing (which may be at a temperature between its glass transition and melting temperature) is pulled over the mandrel shaft, through the die and over the mandrel head by a hauloff device (not shown). The axial force exerted by the tensioning means of the hauloff device causes the tubing to become deformed in the axial direction. Upon reaching the expanding cone of the mandrel head the polymeric material of the tubing is forced to expand in the hoop (radial) direction. This radial deformation is caused by the gradual narrowing of the region between the surface of the mandrel head and the inner wall of the lower region of the die. The amount of radial deformation continues to increase until the tubing reaches the boundary between the cylindrical lower region and conical upper region of the die. Once the tubing crosses this boundary the amount of radial deformation quickly decreases, however, the tubing continues to be deformed in the axial direction. Deformation ceases once the tubing has exited the die and cools below its glass transition temperature.

EXAMPLES

Figure 3:
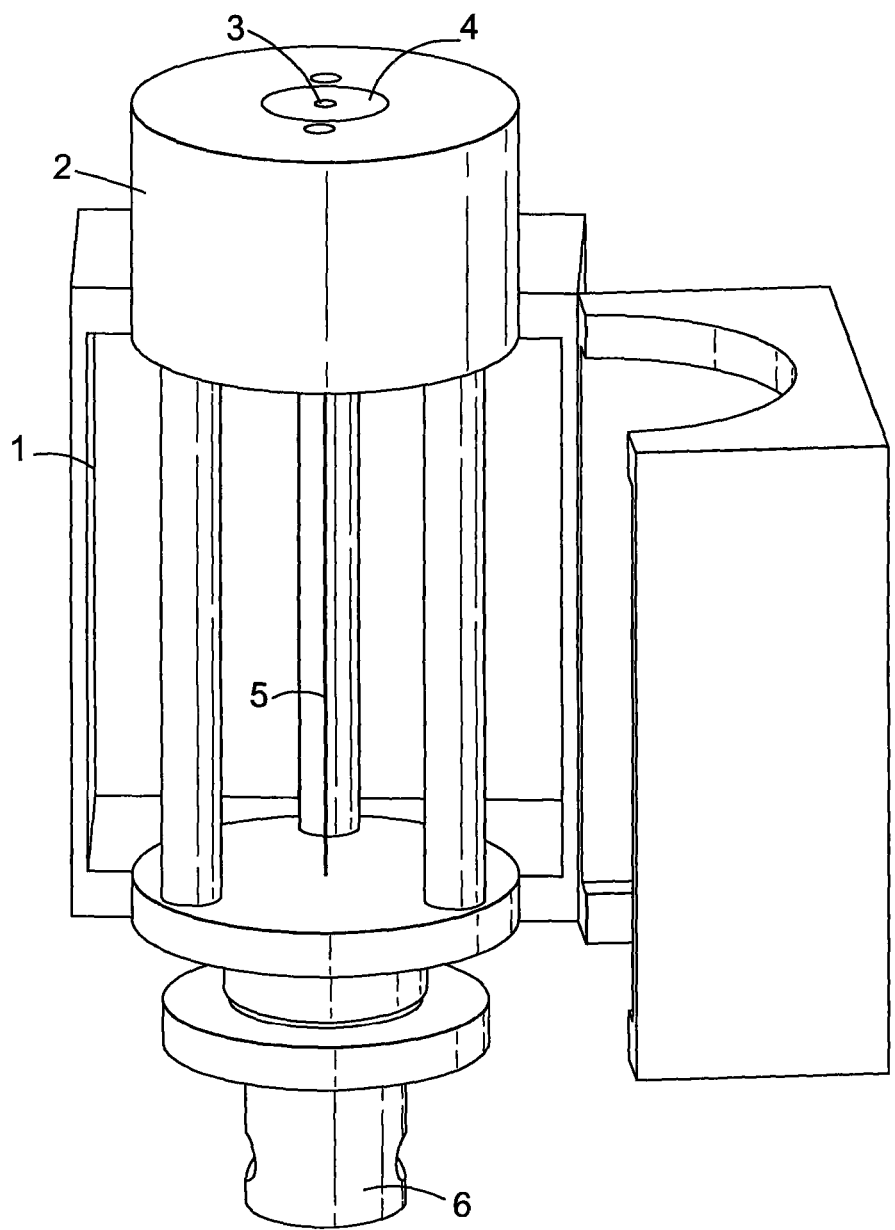
FIG. 3: A schematic diagram showing the apparatus used to conduct the die drawing.

A number of experiments, using an apparatus depicted in FIG. 3, have been conducted to demonstrate that the method of the present invention produces polymeric tubing exhibiting the required characteristics.

The apparatus in FIG. 3 consists of a first (1) and second zones (2) capable of being heated, a mandrel (3), a die (4), a mandrel shaft (5), and a fitting (6) for attaching the apparatus to the base of a tensile test machine.

For these experiments, extruded tubing made from a commercially available grade of PLLA (Purasorb™ PL38) was selected. This grade of polymer is used to produce medical grade tubing for applications such as polymeric stents. PL38 is an extrusion grade of semi-crystalline PLA supplied in the form of uneven pellets which has a melting temperature of 188° C. For the purposes of these experiments, the inventors obtained commercially available extruded tubing supplied by Zeus Inc., USA. The inventors also used non-commercial extruded tubing, which was produced from Purasorb™ PL38 pellets using a laboratory scale single screw extruder (Dr Collin Teachline, screw diameter 16 mm). This extrusion process will now be described in more detail.

Purasorb™ PL38 is a relatively difficult polymer to work with due to its high processing temperature (above 200° C.) and high viscosity. As such, feeding the pellets into the extruder screw was found to be problematic using standard procedures. The inventors found that the extrusion process could be improved by: 1) drying the pellets overnight prior to extrusion; 2) feeding nitrogen gas into the hopper of the extruder to cover the pellets with a blanket of nitrogen gas, thus reducing the chances of oxygen-induced degradation; and 3) cutting the extruded tubing into sections of preferred length and drying them in a nitrogen environment.

The dimensions of the extruded tubes were measured. Specifically, a micrometer was used to measure outer diameter (OD) and pin gauges were used to measure inner diameter (ID). Concentricity and wall thickness were verified using a high resolution flat-bed scanner.

Typical extrusion conditions to produce extruded tubing with preferred characteristics are shown below in Tables 1 to 3:

TABLE 1

Set extruder temperature

|  | Zone 1 | Zone 2 | Zone 3 | Zone 4 | Zone 5 | Zone 6 |
| --- | --- | --- | --- | --- | --- | --- |
| Set temp. (° C.) | 40 | 205 | 210 | 215 | 220 | 220 |

TABLE 2

Die, pin and calibrator dimensions

|  | Die diameter | Pin diameter | Calibrator diameter |
| --- | --- | --- | --- |
| Dimensions (mm) | 5 | 2.5 | 3.0 |

TABLE 3

Set extruder speeds

|  | Screw rotation (rpm) | Haul-off (m/min) | Vacuum pressure (bar) |
| --- | --- | --- | --- |
| Speed | 7.0 | 1.0 | None |

A range of tubes were extruded. The tube dimensions could be controlled by slight variation of extruder screw speed, melt length and haul-off rate. Details of the produced tubes are shown in Table 4 (OD=outer diameter; ID=inner diameter; WT=wall thickness).

TABLE 4

Dimensions of extruded tube following process modifications

| Screw Speed (rpm) | Melt length (mm) | Haul-off speed (m/min) | OD (mm) | ID (mm) | WT (mm) |
| --- | --- | --- | --- | --- | --- |
| 6 | 20 | 1 | 2.4 | 1.2 | 0.6 |
| 7 | 20 | 1 | 2.5 | 1.25 | 0.625 |
| 12 | 50 | 1 | 2.8 | 1.4 | 0.7 |
| 12 | 60 | 1.2 | 2.3 | 1.2 | 0.55 |

Characterisation of Extruded and Die Drawn Tubes in Examples 1 to 3
Tensile Tests In order to compare the mechanical properties of the extruded and die drawn tubes, samples were examined by tensile testing using an Instron tensometer with a 100 N load cell. The test procedure followed that used by Zeus Inc., a commercial medical tubing extrusion company. Extruded tubes of 70 mm length were clamped by directly pinching the ends of between the jaws of the tensometer clamps, using a layer of abrasive paper wrapped round the tube end to improve the grip. Tests were carried out at an extension rate of 50 mm/minute with a grip length of 50 mm. A stress-strain curve was generated from each test using the tube dimensions, deformation rate and measured load, and following parameters were calculated: ultimate tensile strength, elastic modulus, yield strength and extension to break.

Flexural Tests

Flexural properties were also examined using the same tensometer equipped in 3-point bend mode. For each test a sample of tube was supported at two points and a load applied centrally to deform the tube. Load versus extension data was recorded and flexural stress and strain calculated from the recorded data and cross sectional area of the sample.

Crystallinity Tests

In order to determine crystallinity, modulated DSC was conducted between the temperature range of 40° C. to 170° C. Modulation amplitude was set to 0.7° C. with heating rate 5° C./minute and modulation time of 1 minute. Curves for reversible and irreversible heat flow were obtained. Normalised enthalpies of cold crystallisation and re-crystallisation were calculated from exotherms visible on the irreversible heat flow curve, while normalised enthalpy of melting was obtained from integration of the endotherm on the reversible heat flow curve. Percentage crystallinity was calculated using the following equation:

$$\% \text{ Crystallinity} = \frac{\Delta H \text{ melting} - (\Delta H \text{ cold crystallisation} + \Delta H \text{ recrystallisation})}{\Delta H \text{ fusion for } 100\% \text{ crystalline } PLA}$$

The enthalpy of melting of 100% crystalline PLA is 93 J/g.

The following die drawing methods using the apparatus set-up disclosed have been performed by the inventors.

Example 1

The mandrel/die arrangement shown in FIG. 2a was used in this example, with the mandrel being partially within the second heater zone.

The commercially available extruded tube (sourced from Zeus Inc.) had dimensions of 3.00 mm outer diameter, 1.20 mm inner diameter and a wall thickness of 0.90 mm. The parameters used for this set of experiments are shown in Table 5 below:

TABLE 5

| | |
|---|---|
| Start OD (mm) | 3.00 |
| Start ID (mm) | 1.20 |
| Temperature (° C.) | 60-90 |
| Die diameter (mm) [angle (deg)] | 3.3 [15] |
| Mandrel diameter (mm) [angle (deg)] | 2.85 [15] |
| Draw speed (mm/min) | 10-1000 |
| Measured load (N) | 20-80 |
| Drawn OD (mm) | 2.15 |
| Drawn ID (mm) | 1.6 |

The experimental procedure was as follows:
1. An expanded section was produced in a section of extruded tube as described above.
2. Upon solidification, the tube was cut at the location of the expanded section to form a tag.
3. A length of 180 mm tube was fed over the mandrel shaft so that the inflated tag was placed over the mandrel head. The mandrel and mandrel shaft were then placed into temperature controlled oven inside the tensometer so that the mandrel head was located coaxially within the die and the inflated tag was threaded between the mandrel head and the die.
4. The inflated tag was then held in the clamps of the tensometer crosshead (hauloff).
5. The sample of tube was pre-heated in the enclosed first and second heating zones for 10 minutes soak time.
6. After the soak time, the tensometer crosshead was set to extend the sample at a constant speed.
7. The full length of tube was drawn over the mandrel to a final extension length of 500 mm.
8. The drawn tube was cooled under tension for a period of 20 minutes.

Example 1 Results

Tensile Testing

Figure 4:
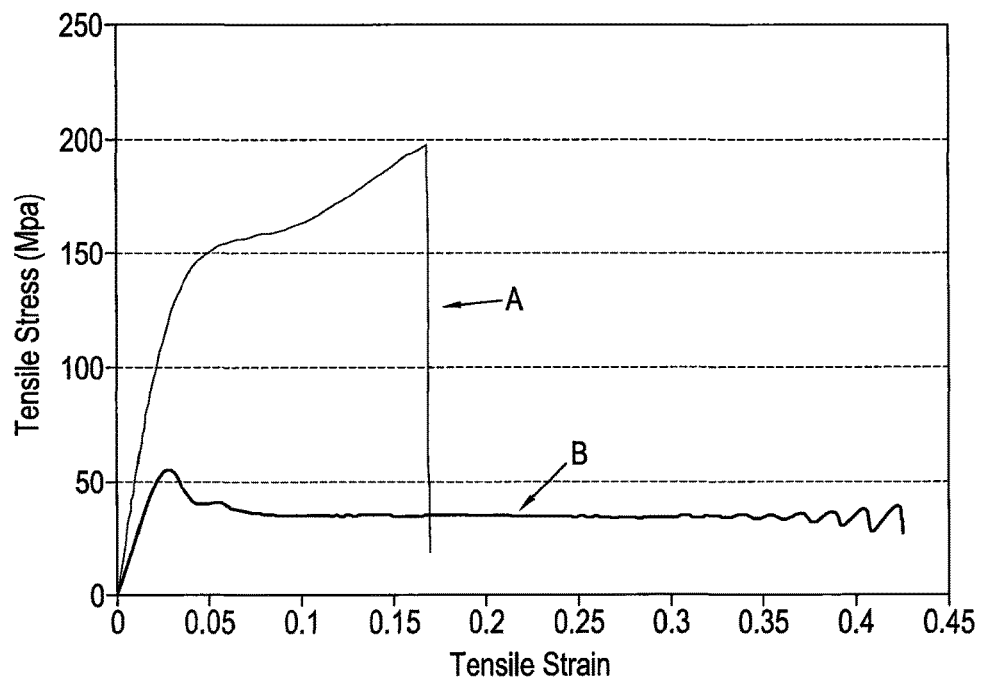
FIG. 4: Tensile test data comparing die drawn (A) and extruded (B) PLLA tube from Example 1.

Typical results from tensile tests of drawn and extruded PLLA tube are displayed in FIG. 4 (A=die drawn tubing; B=extruded tubing). A significant difference between the stress-strain behaviour of drawn and extruded tubes is apparent. The extruded tube deformed elastically to a peak tensile stress of around 50 MPa at approximately 4% extension and then dropped to a constant level of 30 MPa. A strain hardening resonance effect occurred before the sample failed at around 40% extension. The die drawn material exhibited a higher modulus (gradient) in the elastic region before reaching an initial peak (yield) stress of around 160 MPa. At higher strains above 20% extension the stress increased linearly up to around 195 MPa before failing at ~17% extension.

As shown in Table 6, the tensile yield strength increased after die drawing by around 190%. Ultimate (maximum) tensile strength increased by 250% above the value of extruded tube. Tensile modulus was found to decrease after die drawing by around 61%.

TABLE 6

Tensile test results comparing extruded and die drawn PLLA tube (average of 5 tests; standard deviation shown in brackets).

| | Tensile testing results (Mean ± Standard error) | | | |
|---|---|---|---|---|
| Sample | Tensile modulus (MPa) | Yield strength (MPa) | Ultimate tensile strength (MPa) | Elongation at break (%) |
| Extruded tubes | 2708 ± 12.08 | 55.03 ± 0.81 | 55.03 ± 0.81 | 51.80 ± 9.22 |
| Drawn tubes (Example 1) | 4362 ± 92.26 | ~160 | 194.20 ± 4.20 | 16.55 ± 0.50 |

Flexural Results

Figure 5:
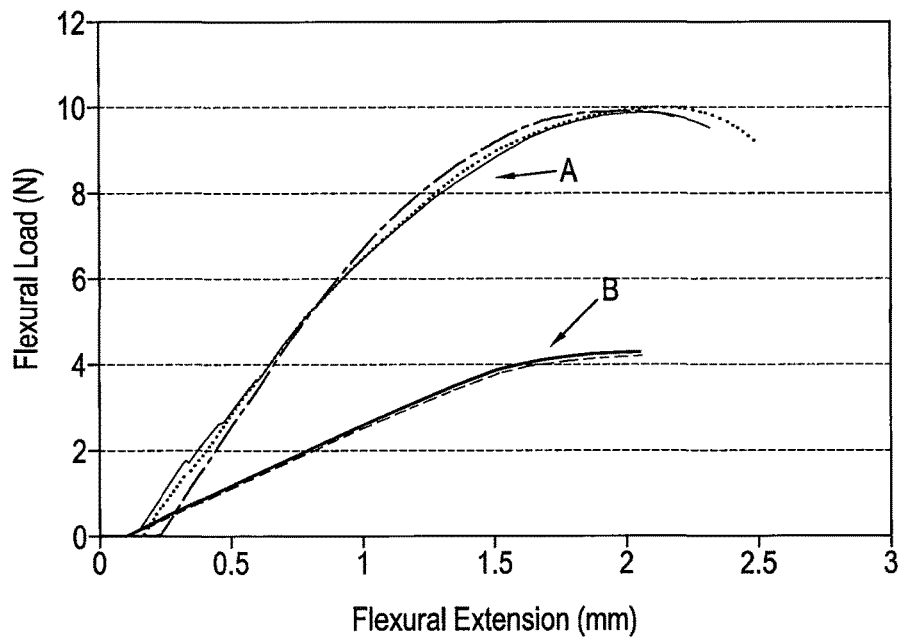
FIG. 5: Flexural test results comparing die drawn tube (A) (OD: 2.0, ID: 1.8 mm) and Zeus extruded tube (B) (OD 1.6 mm, ID 1.0 mm).

Typical results from flexural tests of drawn and extruded PLLA tube are displayed in FIG. 5 (A=die drawn tubing; B=extruded tubing).

In conclusion, the batch die drawing method of Example 1 produced oriented small bore PLLA tubing with a draw ratio of approximately 3:1 at temperatures of 60-80° C. The tensile yield strength of the die drawn tube was approximately 190% higher than that of the extruded tube and maximum tensile strength was approximately 250% higher. The tensile modulus increased by approximately 61% compared to that of the extruded tube. This study shows that significant improvements in the mechanical properties of PLLA tube can be achieved by using the die drawing process on polymeric tubes that are capable of being used to form stents.

Example 2

The commercially available extruded tube (sourced from Zeus Inc.) had dimensions of 1.6 mm outer diameter, 1.0 mm inner diameter and a wall thickness of 0.3 mm. The parameters used for this set of experiments are shown in Table 7 below:

TABLE 7

| | |
|---|---|
| Start OD (mm) | 1.6 |
| Start ID (mm) | 1.0 |
| Temperature (° C.) | 65 |
| Die diameter (mm) [angle (deg)] | 3.0 [15] |
| Mandrel diameter (mm) [angle (deg)] | 2.2 [15] |
| Draw speed (mm/min) | 50-70 |
| Measured load (N) | ~25 |
| Dwell prior to test (mins) | 5 |
| Dwell post test (mins) | 10 |
| Drawn OD (mm) | 1.85 |
| Drawn ID (mm) | 1.65 |

The experimental procedure was as follows:
1. A tag was produced in the end section of extruded tube by heating a small section of tube and blowing air across it.
2. Upon solidification, the tube was cut at the location of the bubble to form a tag.
3. A length of 180 mm tube was fed over the mandrel shaft so that the inflated tag was placed over the mandrel head. The mandrel and mandrel shaft were then placed into temperature controlled oven (first and second heating zones) inside the tensometer so that the mandrel head was located coaxially within the die and the inflated tag was threaded between the mandrel head and the die.
4. The inflated tag was then held in the clamps of the tensometer crosshead (hauloff).
5. The sample of tube was pre-heated in the enclosed first and second heating zones for 5 minutes soak time.
6. After the soak time, the tensometer crosshead was set to extend the sample at a constant speed.
7. The full length of tube was drawn over the mandrel to a final extension length of 500 mm.
8. The drawn tube was cooled under tension for a period of 10 minutes.

Example 2 Results
Tensile Testing

Figure 6:
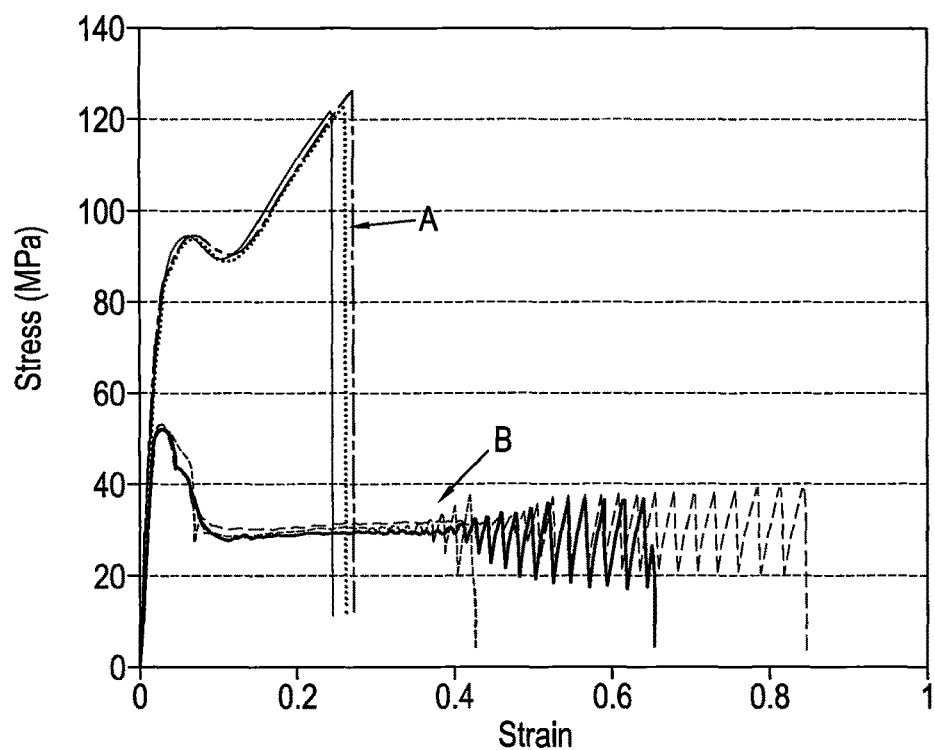
FIG. 6: Tensile test data comparing die drawn (A) and extruded (B) PLLA tube from Example 2.

Typical results from tensile tests of the die drawn tube of Example 2 and extruded PLLA tube are displayed in FIG. 6 (A=die drawn tubing; B=extruded tubing). A significant difference in the stress-strain behaviour of the two tubes is apparent. The extruded tube deformed elastically to a peak tensile stress of around 50 MPa at approximately 4% extension and then dropped to a constant level of 30 MPa. A strain hardening resonance effect occurred before the sample failed at between 40% and 85% extension. The die drawn material exhibited higher values of modulus (gradient) in the elastic region before reaching an initial peak (yield) stress at around 95 MPa. At higher strains above 15% extension the stress increased linearly up to around 125 MPa before failing at ~30% extension.

Average results from 3 samples of each tube are summarised in Table 8. Tensile yield strength increased after die drawing by 71%. Ultimate (maximum) tensile strength increased by 136% above the value of extruded tube. Tensile modulus was found to increase after die drawing by around 23%. Elongation at break was reduced by around 60% following die drawing.

TABLE 8

Tensile test results comparing extruded and die drawn PLA tube.

| | Tensile testing results (Mean ± Standard error) | | | |
| --- | --- | --- | --- | --- |
| Sample | Tensile modulus (MPa) | Yield strength (MPa) | Ultimate tensile strength (MPa) | Strain at break |
| Extruded tubes | 2649.47 ± 17.71 | 55.41 ± 0.66 | 52.17 ± 0.38 | 0.64 ± 0.12 |
| Drawn tubes (Example 2) | 3259.97 ± 15.33 | 94.15 ± 0.32 | 123.38 ± 2.36 | 0.26 ± 0.01 |

The values of elastic modulus and ultimate tensile strength are lower than some of the values previously reported in this project for die drawn tube. This is because the dimensions of the drawn tube used here were 2.33 mm OD and 1.66 mm ID giving a wall thickness of 0.335 mm.

Flexural Testing

Figure 7:
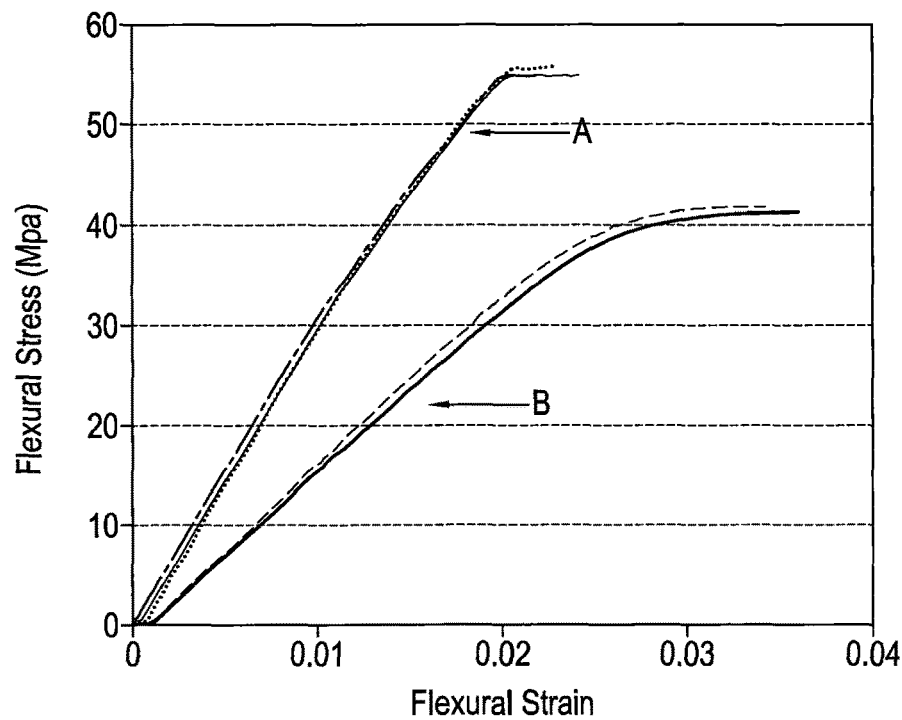
FIG. 7: Flexural test data comparing die drawn (A) and extruded (B) PLLA tube from Example 2.

Results from flexural (3 point bending) test data are displayed in FIG. 7 (A=die drawn tubing; B=extruded tubing). The die drawn tube of Example 2 exhibited a 79% higher flexural modulus than that of the extruded tube. Flexural strength, defined by the plateau of flexural stress was also higher for drawn tube by 34%. These results are summarised in Table 9.

TABLE 9

Flexural test results comparing extruded and die drawn PLA tube

| | Tensile testing results (Mean ± Standard error) | | |
| --- | --- | --- | --- |
| Sample | Flexural modulus (MPa) | Flexural strength (MPa) | Flexure strain at stress plateau |
| Extruded tubes | 1712.13 ± 23.30 | 41.053 ± 0.046 | 0.0299 ± 0.000795 |
| Drawn tubes (Example 2) | 3070.73 ± 51.28 | 54.953 ± 0.332 | 0.0198 ± 0.000405 |

Crystallinity Testing

From the results of modulated DSC experiments, values of crystallinity for extruded tubes were found to be 13.75±1.94 (mean±standard error), while for die drawn tubes this increased to 40.94±4.83. This significant increase in crystallinity is likely to result from the raised temperature to which the tube was exposed to during testing and from strain induced crystallisation during the die drawing process.

Example 3

The commercially available extruded tube (sourced from Zeus Inc.) had dimensions of 3.0 mm outer diameter, 1.2 mm inner diameter and a wall thickness of 0.9 mm. The parameters used for this set of experiments are shown in Table 10 below:

TABLE 10

| | |
| --- | --- |
| Start OD (mm) | 3 |
| Start ID (mm) | 1.2 |
| Temperature (° C.) | 80 |
| Die diameter (mm) | 3.3 |
| Die semi angle (degrees) (Die entry semi angle) | 15 |
| Mandrel diameter (mm) | 2.85 |
| Mandrel cone (degrees) | 15 |
| Draw speed (mm/min) | 900 |
| Measured load (N) | 30-40 |
| Dwell prior to test (mins) | 10 |
| Drawn OD (mm) | 2.15 |
| Drawn ID (mm) | 1.6 |

The experimental procedure was as follows:
1. A tag was produced in a section of extruded tube by applying air pressure and heating a small section of tube.
2. Upon solidification, the tube was cut at the location of the bubble to form a tag.
3. A length of 180 mm tube was fed over the mandrel shaft so that the inflated tag was placed over the mandrel head. The mandrel and mandrel shaft were then placed into temperature controlled oven (first and second heating zones) inside the tensometer so that the mandrel head was located coaxially within the die and the inflated tag was threaded between the mandrel head and the die.
4. The inflated tag was then held in the clamps of the tensometer crosshead (hauloff).
5. The sample of tube was pre-heated in the enclosed first and second heating zones that were at 80° C. for 10 minutes soak time.
6. After the soak time, the drawing speed of the tensometer crosshead was gradually increased up to a speed of 900 mm/min.

7. The full length of tube was drawn over the mandrel to a final extension length of 500 mm.
8. The drawn tube was cooled under tension.

Die Drawing Experiments

When using die drawn tubing to produce stents, it is preferable that the outer diameter of the drawn tube is about 2.0 mm and the inner diameter is about 1.8 mm, thus giving a wall thickness of about 0.1 mm (100 microns). A series of die drawing experiments were performed using a selected range of mandrel geometries, draw speeds and set temperatures to investigate the relationship between certain draw parameters and final drawn tube dimensions, with a view to achieving the preferred tube dimensions. The extruded tube used in these experiments was produced by the inventors using a single screw extrusion method described previously. The extruded tube had an outer diameter of 2.65 mm and an inner diameter of 1.20 mm.

A die drawing rig as depicted in FIG. 3 was used to carry out these experiments and a draw temperature of 85° C. was used for all of the experiments. The general experimental procedure was as follows:

1. A bubble was produced in a section of extruded tube by applying air pressure and heating a small section of tube.
2. Upon solidification, the tube was cut at the location of the bubble to form a tag.
3. A length of 180 mm tube was loaded into the temperature controlled oven inside the tensometer with the inflated tag placed over the mandrel.
4. After 5 minutes soak time, the tensometer crosshead was set to extend the sample at a constant speed.
5. The full length of tube was drawn over the mandrel to a final extension length of 500 mm.
6. The drawn tube was under tension to cool for a period of 10 minutes.

Results of Die Drawing Experiments

Figure 8:
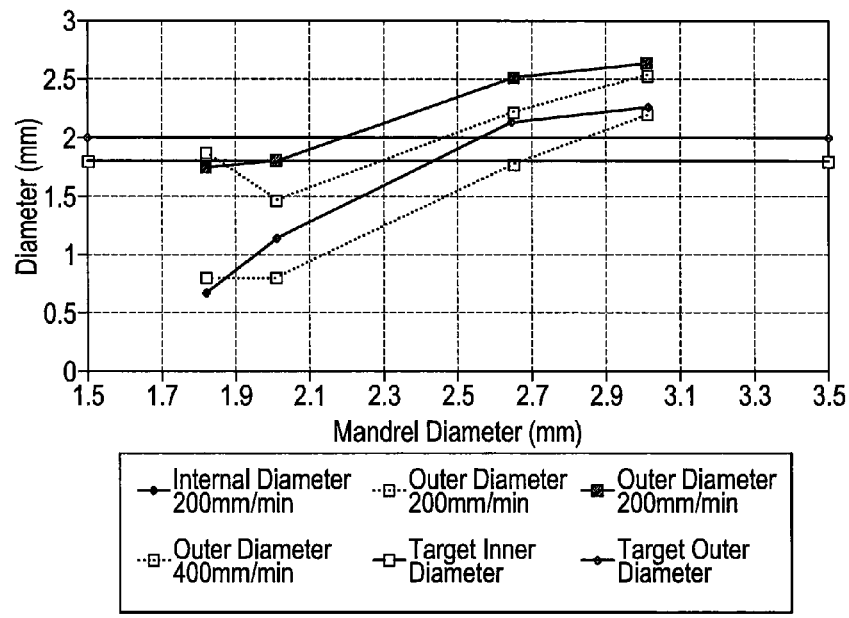
FIG. 8: A plot showing the relationship between the inner and outer diameter of die drawn tubing and mandrel diameter at different draw speeds. Target inner diameter=1.8 mm; target outer diameter=2.0 mm.

FIG. 8 shows how the inner and outer diameter of the drawn tube varies depending on the diameter of the mandrel and the draw speed, and the results are summarised in Table 11. The results suggest that a mandrel diameter of between 1.8 mm and 2.6 mm and draw speeds of between 100 mm/min and 300 mm/min are preferable in order to achieve the target tube dimensions of 2.0 mm OD and 1.8 mm ID.

TABLE 11

| Mandrel (mm) | Temp (° C.) | Draw Speed (mm/min) | ID (mm) | OD (mm) | WT (mm) |
| --- | --- | --- | --- | --- | --- |
| 3.01 | 85 | 200 | 2.54 | 2.84 | 0.15 |
| 3.01 | 85 | 400 | 2.44 | 2.74 | 0.15 |
| 2.65 | 85 | 200 | 2.36 | 2.67 | 0.155 |
| 2.65 | 85 | 400 | 2.14 | 2.48 | 0.17 |
| 2.01 | 85 | 200 | 1.18 | 1.86 | 0.34 |
| 2.01 | 85 | 400 | 0.9 | 1.58 | 0.34 |
| 1.82 | 85 | 200 | 1.08 | 2.6 | 0.76 |
| 1.82 | 85 | 400 | 1.08 | 2.58 | 0.75 |

The following example was conducted using the preferred ranges of mandrel diameter and draw speed which were identified in the die drawing experiments.

Example 4

The mandrel/die arrangement shown in FIG. 2b was used in this example, with the mandrel being partially within the second heater zone to give a draw temperature of 85° C. The experimental procedure was as follows:

1) An expanded section was produced in a section of extruded tube as described above.
2) Upon solidification, the tube was cut at the location of the expanded section to form a tag.
3) A length of 180 mm tube was fed over the mandrel shaft so that the inflated tag was placed over the mandrel head. The mandrel and mandrel shaft were then placed into a temperature controlled oven inside the tensometer so that the mandrel head was located coaxially within the die and the inflated tag was threaded between the mandrel head and the die.
4) The inflated tag was then held in the clamps of the tensometer crosshead (hauloff).
5) The sample of tube was pre-heated in the enclosed first and second heating zones for 10 minutes soak time.
6) After the soak time, the tensometer crosshead was set to extend the sample at a constant speed.
7) The full length of tube was drawn over the mandrel to a final extension length of 500 mm.
8) The drawn tube was cooled under tension for a period of 20 minutes.

The parameters used for this set of experiments and the resultant drawn tube dimensions are shown in Table 12 below.

The die drawn tubing of Examples 4a, 4b and 4c were produced from non-commercial extruded PLLA tubing, whereas the die drawn tubing of Examples 4d and 4e were produced from commercial extruded PLLA tubing supplied by Zeus Inc., USA.

TABLE 12

| | Example No. | | | | |
| --- | --- | --- | --- | --- | --- |
| | 4a | 4b | 4c | 4d | 4e |
| Start OD (mm) | 2.37 | 2.37 | 2.4 | 2.36 | 2.37 |
| Start ID (mm) | 1.26 | 1.26 | 1.24 | 1.20 | 1.26 |
| Start WT (mm) | 0.56 | 0.58 | 0.58 | 0.58 | 0.58 |
| Temperature (° C.) | 85 | 85 | 85 | 85 | 85 |
| Die entry diameter (mm) [angle (deg)] | 2.75 [30] | 2.75 [30] | 2.75 [30] | 2.75 [30] | 2.75 [30] |
| Mandrel diameter (mm) [angle (deg)] | 1.84 [30] | 2.01 [30] | 2.18 [30] | 1.85 [30] | 2.20 [30] |
| Draw speed (mm/min) | 100 | 200 | 100 | 200 | 300 |
| Drawn OD (mm) | 2.00 | 2.14 | 2.28 | 2.00 | 2.22 |
| Drawn ID (mm) | 1.70 | 1.86 | 2.04 | 1.70 | 1.94 |
| Drawn WT (mm) | 0.15 | 0.14 | 0.12 | 0.15 | 0.14 |

Characterisation of Die Drawn Tubes in Example 4

Tensile Tests

Samples of extruded and drawn tube were examined by tensile testing using an Instron tensometer with a 100 N load cell. The test procedure followed that used by Zeus Inc., a commercial medical tubing extrusion company, although the clamping method had to be developed to ensure that the drawn tube did not slip and failed in the gauge length rather than at the grips. A tube length of 90 mm was used and two closely fitting pin gauges were inserted into each end of the tube so that they met at the centre. Specially modified clamps were made to incorporate the radius of the tube. Tests were carried out at an extension rate of 5 mm/minute with a gauge length of 30 mm. A stress-strain curve was generated from each test using the tube dimensions, deformation rate and measured load, and the following parameters were calculated: ultimate tensile strength; elastic modulus; yield strength; and extension to break. This method was found to be suitable for both extruded and drawn tubes.

Flexural Tests

Flexural properties were also examined using the same tensometer in 3-point bend mode. For each test a sample of tube was supported at two points, 25 mm apart and a compressive load was applied centrally to deform the tube at a rate of 1 mm/min. Load versus extension data was recorded and flexural stress and strain calculated from the recorded data and tube dimensions.

Hoop Tests

A jig was designed and manufactured to test the hoop strength of extruded and die drawn tube. The test specimen was a ring of tubing with four notches for hoop strength testing, which was cut as a slice from the die drawn tube. The testing specimens had a width of 2 mm, and two two-sided notches, with a distance of 1.0 mm between the notches (similar to the testing specimens used in US 2010/0025894 A1). Tests were performed at an extension rate of 5 mm/min.

Crystallinity Tests

The same test was used as that used to test the crystallinity of the tubing of Examples 1 to 3.

Example 4 Results

Tensile Testing

Figure 9:
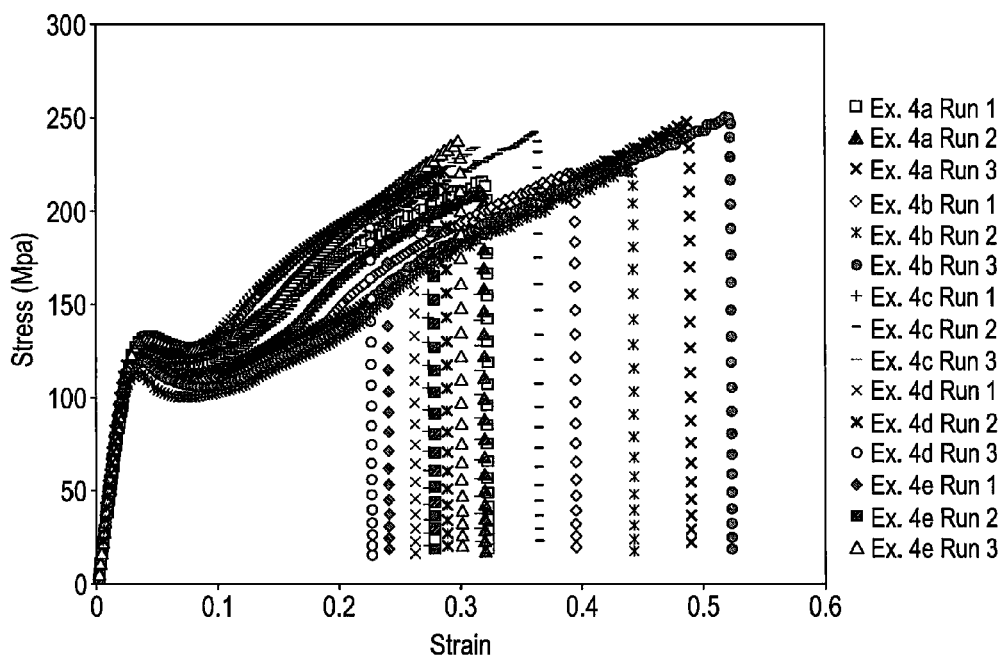
FIG. 9: Tensile test data comparing die drawn non-commercial extruded tubing (Examples 4a to 4c) and die drawn commercial (Zeus) extruded tubing (Examples 4d and 4e).

The results of the tensile testing of the drawn tubes from Example 4 are displayed in FIG. 9 and summarised in Table 13. All samples exhibited similar behaviour in the linear (elastic) region of deformation. Yield occurred at a tensile stress between 110 and 130 MPa for all of the samples, and failure occurred within a tensile stress range of between 200 and 250 MPa.

The strain at break was lower for the samples of Examples 4d and 4e (die drawn commercial tubing) than for the samples of Examples 4a and 4c (die drawn non-commercial tubing). The highest strain at break was measured for samples of Examples 4a and 4b, having wall thickness of 0.14 mm and 0.15 mm, respectively.

The tensile properties of all samples were comparable. The highest tensile modulus and ultimate tensile strength (UTS) were measured for Examples 4b and 4c whereas highest yield strength was observed for Examples 4d and 4e.

TABLE 13

Tensile test results comparing die drawn non-commercial extruded PLLA tubing (Examples 4a, 4b and 4c) from die drawn commercial (Zeus) extruded PLLA tubing (Examples 4d and 4e). The values are averages of 3 repeat experiments.

| Sample | Yield Strength (MPa) | UTS (MPa) | Tensile Modulus (MPa) | Strain at break |
|---|---|---|---|---|
| Example 4a | 124.2 | 225.5 | 5155.4 | 0.37 |
| Example 4b | 117.7 | 231.7 | 5242.9 | 0.45 |
| Example 4c | 126.9 | 230.3 | 5324.5 | 0.31 |
| Example 4d | 128.5 | 210.4 | 4833.1 | 0.29 |
| Example 4e | 128.4 | 222.3 | 5019.8 | 0.27 |

Flexural Testing

Figure 10:
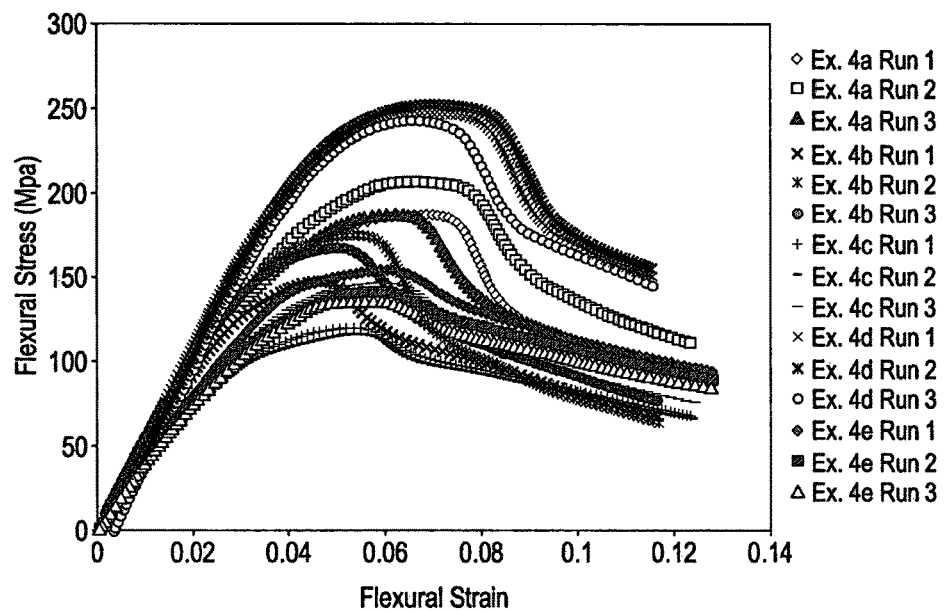
FIG. 10: Flexural test data comparing die drawn non-commercial extruded tubing (Examples 4a to 4c) and die drawn commercial (Zeus) extruded tubing (Examples 4d and 4e).

Results from 3 point bending tests are shown in FIG. 10 and summarised in Table 14. All samples exhibited similar behaviour in bending, although there was a significant variation in flexural strength, which was found to be dependent primarily on wall thickness. The flexural modulus ranged from 3965 to 5999 MPa. The drawn tubing of Example 4d exhibited the highest flexural strength and the highest flexural modulus.

TABLE 14

Flexural test results comparing die drawn non-commercial extruded PLLA tubing (Examples 4a, 4b and 4c) from die drawn commercial (Zeus) extruded PLLA tubing (Examples 4d and 4e). The values are averages of 3 repeat experiments.

| Sample | Flexural Modulus (MPa) | Flexural Strength (MPa) |
|---|---|---|
| Example 4a | 4749.6 | 194.1 |
| Example 4b | 5280.2 | 163.1 |
| Example 4c | 3965.2 | 127.8 |
| Example 4d | 5998.7 | 247.6 |
| Example 4e | 4058.4 | 144.0 |

Hoop Strength Testing

Figure 11:
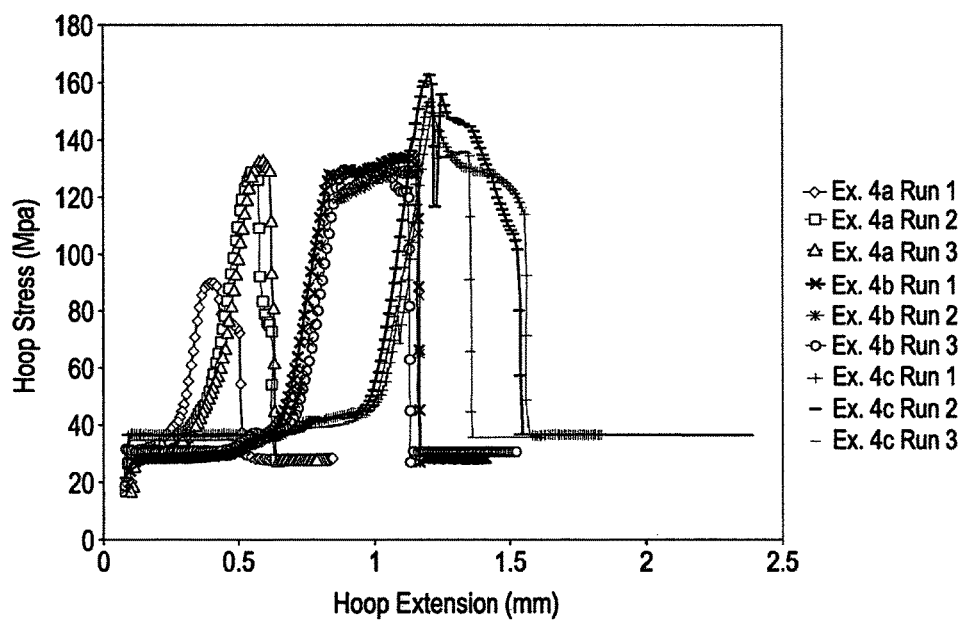
FIG. 11: Hoop test data for the die drawn tubes of Examples 4a to 4c.

Measurement of hoop strength was only possible for die drawn non-commercial extruded PLLA tubing (Examples 4a, 4b and 4c) as these were the only tubes which had been laser cut into the required geometry. The results of these tests are shown in FIG. 11 and summarised in Table 15. Due to the size of the sample of drawn tubing used for this test (a 0.5 mm ring with two semi-circular cut outs) the sample was not pre-tensioned during the test. This explains why there is a delay before stress began to rise for some samples shown in FIG. 11. All samples exhibited a linear rise in stress before reaching a peak. Due to the round geometry of the narrow section of the test specimens it was not possible to calculate modulus.

The results in Table 15 show that hoop strength (both yield and ultimate strength) increased as wall thickness of the drawn tube decreased. This suggests that the hoop strength was proportional to the draw ratio imparted to the tube.

TABLE 15

Hoop test results for die drawn non-commercial extruded PLLA tubing (Examples 4a, 4b and 4c)

| Sample | Hoop Yield Strength (MPa) | Ultimate Hoop Strength (MPa) |
|---|---|---|
| Example 4a | 112.1 | 117.3 |
| Example 4b | 124.1 | 131.3 |
| Example 4c | 149.5 | 155.8 |

These measurements of hoop strength can be directly compared to those presented in US 2010/0025894 A1, which details the tube expansion process developed by Abbott Cardiovascular Inc. The ultimate hoop strength of the die drawn tubing produced by the method of the present invention (117 to 156 MPa) is higher than the ultimate hoop strength of radially expanded tubing of US 2010/0025894 A1 (75 to 116 MPa).

Crystallinity Testing

The results from modulated DSC tests are displayed in Table 16. Crystallinity values ranged from 37 to 47%, The die drawn tubing of Examples 4d and 4e exhibited approximately 5% higher crystallinity die drawn tubing of Examples 4a and 4b, respectively.

TABLE 16

Measured crystallinity of die drawn non-commercial extruded PLLA tubing (Examples 4a, 4b and 4c) and die drawn commercial (Zeus) extruded PLLA tubing (Examples 4d and 4e).

| Sample | Crystallinity (%) | Standard Deviation (%) |
|---|---|---|
| Example 4a | 36.7 | 0.92 |
| Example 4b | 41.4 | 0.23 |
| Example 4c | 44.8 | 0.25 |
| Example 4d | 41.0 | 1.02 |
| Example 4e | 46.6 | 0.36 |

Comparison of Die Drawn Tubing with Extruded Tubing

The physical properties of the die drawn tubing from Examples 4a-4e were compared with the physical properties of: A) non-commercial extruded PLLA tubing (Comparative Example 1); and B) commercial (Zeus) extruded PLLA tubing (Comparative Example 2). The tubing of Comparative Example 1 had a wall thickness of 0.575 mm (OD: 2.35 mm; ID 1.2 mm) and the tubing of Comparative Example 2 had a wall thickness of 0.59 mm (OD: 2.38 mm; ID 1.2 mm). The results are summarised in Table 17.

TABLE 17

Summary of the physical properties of extruded tubing (Comparative Examples 1 and 2) and die drawn tubing (Examples 4a to 4e)

| Sample | UTS (MPa) | Tensile Modulus (MPa) | Strain to break | Flexural Modulus (MPa) | Hoop Strength (MPa) | Crystallinity (%) |
|---|---|---|---|---|---|---|
| Comparative Example 1 | 64.2 | 2929.0 | 0.12 | 3676.4 | — | 9.6 |
| Comparative Example 2 | 69.9 | 2949.4 | 0.12 | 3683.9 | — | 13.8 |
| Example 4a | 225.5 | 5155.4 | 0.37 | 4453.8 | 117.3 | 36.7 |
| Example 4b | 231.7 | 5242.9 | 0.45 | 4550.1 | 131.3 | 41.4 |
| Example 4c | 230.3 | 5324.5 | 0.31 | 3018.8 | 155.8 | 44.8 |
| Example 4d | 210.4 | 4833.1 | 0.29 | 5998.7 | — | 41.0 |
| Example 4e | 222.3 | 5019.8 | 0.27 | 3438.8 | — | 46.6 |

There was a notable increase in the tensile modulus. The most significant change occurred in ultimate tensile strength, which increased by a factor of 3-4 after die drawing. Hoop strength was not measured for Comparative Examples 1 and 2.

It will be appreciated that it is not intended to limit the present invention to the above examples only, other embodiments being readily apparent to one of ordinary skill in the art without departing from the scope of the appended claims.

Other aspects of the invention include the following:

Aspects

Aspect 1. A method of producing a tube for use in the formation of a stent, said method comprising:
deforming an orientable, thermoplastic polymer tubing in the solid phase by drawing it over a mandrel and/or through a die, where the mandrel has a lead end and an exit end and the die has an entry side and an exit side, wherein:
a drawing mechanism applies a drawing tension to the tubing from the exit end of the mandrel and/or the exit side of the die, said tension being insufficient to cause tensile failure of the tubing but sufficient to deform the tubing, thereby drawing the tubing over the mandrel and/or through the die in the solid phase to induce uniaxial or biaxial orientation of the polymer; and
collecting the deformed tubing from the exit end of the mandrel and/or the exit side of the die.

Aspect 2. A method according to Aspect 1, wherein the orientable, thermoplastic polymer tubing is at a temperature above the glass transition temperature and below the melting temperature of the thermoplastic polymer.

Aspect 3. A method according to Aspect 1 or 2, wherein the resultant wall thickness of the tube is between 75 and 150 microns.

Aspect 4. A method according to any one of Aspects 1 to 3, wherein the bulk cross-sectional area of the polymeric tubing is reduced by drawing said tubing over the mandrel and/or through the die.

Aspect 5. A method according to any one of Aspects 1 to 4, wherein the orientable, thermoplastic polymer tubing has a tag portion and the drawing mechanism comprises a haul-off comprising a gripping mechanism in which the tag portion is gripped.

Aspect 6. A method according to any one of Aspects 1 to 5, wherein the thermoplastic polymer tubing has been extruded from a polymer melt.

Aspect 7. A method according to any one of Aspects 1 to 6, wherein the thermoplastic polymer tubing is bioresorbable.

Aspect 8. A method according to any one of Aspects 1 to 7, wherein the thermoplastic polymer is albumin, collagen, hyaluronic acid and derivatives thereof, sodium alginate and derivatives thereof, chitosan and derivatives thereof, gelatin, starch, cellulose polymers, casein, dextran and derivatives thereof, polysaccharides, fibrinogen, poly (valerolactone), polydioxanone, and copolymers of lactide and 1,4-dioxane-2-one, poly(hydroxybutyrate), poly(hydroxyvalerate), poly(hydroxybutyrate-co-hydroxyvalerate) copolymers, poly(alkylcarbonate), poly(orthoesters), tyrosine based polycarbonates and polyarylates, poly(ethylene terephthalate), poly(anhydrides), poly(ester-amides), polyphosphazenes, poly (amino acids), poly-L-lactic acid (PLLA), poly-D,L-lactic acid (PDLLA), polyglycolic acid (PGA), copolymers of polylactic acid, polyglycolic acid (PLGA), polycaprolactone, poly (4-hydroxybutyrate) (P4HB), polydioxanone, poly (trimethylene carbonate), poly (hydroxybutyrate-hydroxyvalerate), polyorthoester; poly(ester amides), poly (ortho esters), polyanhydrides, poly (anhydride-co-imide), poly (propylene fumarate), pseudo poly (amino acid), poly (alkyl cyanoacrylates), polyphosphazenes, and polyphosphoester.

Aspect 9. A method according Aspect 8, wherein the thermoplastic polymer is Poly (L-lactide) Poly (D,L-lactide), or Poly(glycolide).

Aspect 10. A method according to any one of Aspects 1 to 9, wherein the diameter of the mandrel at its widest point is from 0.01 to 15 mm.

Aspect 11. A method according to Aspect 9, wherein the lead end of the mandrel is tapered and/or the exit end of the mandrel is tapered.

Aspect 12. A method according to Aspect 9, wherein the mandrel is an expanding cone mandrel.

Aspect 13. A method according to Aspects 11 or 12, wherein the angle of inclination of the taper is from 5 to 60 degrees, optionally wherein the angle of inclination of the taper is from 20 to 40 degrees.

Aspect 14. A method according to any one of Aspects 1 to 13, wherein the entry side of the die has a diameter from 0.4 to 8.0 mm and/or the exit side of the die has a diameter from 1.0 to 15 mm, optionally wherein the entry side of the die has a diameter from 2.0 to 4.0 mm.

Aspect 15. A method according to any one of Aspects 1 to 14, wherein the die is selected from: a conical die; a converging (reducing) die; a diverging (expanding) die; and a parallel (sizing) die, optionally wherein the die is a diverging die.

Aspect 16. A method according to any one of Aspects 1 to 15, wherein the semi angle of the die entry and/or exit is from 0 to 50 degrees, optionally wherein the semi angle is from 20 to 40 degrees.

Aspect 17. A method according to any one of Aspects 10 to 16, wherein the ratio of the die entry or exit angle and the angle of inclination of the mandrel taper is in the range of 1:1 to 10:1, optionally in the range of 1:1 to 5:1.

Aspect 18. A method according to any one of Aspects 1 to 17, wherein the mandrel and/or the die is/are maintained at a temperature between the glass transition temperature and the melting temperature of the polymer used in the orientable, thermoplastic polymer tubing.

Aspect 19. A method according to any one of Aspects 1 to 18, wherein the draw speed is from 0.00001 to 15000 mm min$^{-1}$.

Aspect 20. A method according to any one of Aspects 1 to 19, wherein the inner hoop draw ratio is at least 1.5.

Aspect 21. A method according to any one of Aspects 1 to 20, wherein the axial draw ratio is from 1.5:1 to 15:1.

Aspect 22. A method according to Aspect 21, wherein the axial draw ratio is from 2.5:1 and 4:1.

Aspect 23. A method according to any one of Aspects 1 to 22, wherein the ratio of the axial draw ratio to the inner hoop draw ratio is in the range of 0.5:1 to 10:1.

Aspect 24. A method according to any one of Aspects 1 to 23, further comprising the step of extruding the thermostatic polymeric tubing from an upstream extruder prior to the deformation step.

Aspect 25. A method according to any one of Aspects 1 to 24, further comprising pre-heating the thermostatic polymer tubing to a temperature between the glass transition temperature and melting temperature of the polymer, wherein the tubing is maintained at said temperature for 1 to 60 minutes prior to deformation.

Aspect 26. A method according to Aspect 25, wherein the temperature is maintained for 2 to 10 minutes.

Aspect 27. A method according to any one of Aspects 1 to 26, wherein the cooling of the orientable, thermoplastic polymer tubing starts while in contact with the die and/or mandrel or immediately after said tubing has been drawn over the mandrel and/or through the die.

Aspect 28. A method according to any one of Aspects 1 to 27, wherein the method comprises the use of both the die and the mandrel.

Aspect 29. A method according to any one of Aspect 1 to 28, wherein the crystallinity of the resulting tubing is from 5% to 90%, optionally from 30% to 70%.

Aspect 30. A method according to any one of Aspects 1 to 29, wherein the method is continuous.

Aspect 31. A method according to any one of Aspects 1 to 30, wherein the orientable, thermoplastic polymer tubing for use in said method has an inner diameter from 0.5 mm to 4.0 mm, and an outer diameter from 0.9 mm and 15 mm.

Aspect 32. A method according to any one of Aspects 1 to 31, wherein the orientable, thermoplastic polymer tubing for use in said method has a wall thickness of 0.1 mm to 1.0 mm.

Aspect 33. A method according to any one of Aspects 2 to 32, wherein the temperature is from about 75° C. to about 95° C., optionally wherein the temperature is about 85° C.

Aspect 34. A method according to any one of Aspects 1 to 33 further comprising preparing a stent from a tubing subjected to the processes of said aspects.

Aspect 35. A tube for use in a stent comprising a polymeric material having a wall thickness that is from 75 microns to 150 microns, optionally wherein the tube has a tensile modulus from 2,500 to 6,000 MPa and a tensile yield strength from 90 to 600 MPa.

Aspect 36. The tube of Aspect 35, wherein the polymeric material is bioresorbable and the breakdown products are biocompatible.

Aspect 37. The tube of Aspect 35 or Aspect 36, wherein the polymeric material is oriented in the axial and radial directions of the tube.

Aspect 38. The tube of Aspect 37, wherein the tubing has been subjected to orientation by die drawing with a mandrel and/or a die.

Aspect 39. The tube of any one of Aspects 35 to 38, wherein the ultimate tensile strength is from 120 to 800 MPa.

Aspect 40. The tube of any one of Aspects 35 to 39, wherein the tube has an inner diameter from 0.5 to 4.0 mm and an outer diameter from 1.5 mm to 15 mm.

Aspect 41. The tube of any one of Aspects 35 to 40, wherein the wall thickness is 100 microns.

Aspect 42. The tubing of any one of Aspects 35 to 41 wherein the polymeric material is: albumin; collagen; hyaluronic acid and derivatives thereof; sodium alginate and derivatives thereof; chitosan and derivatives thereof; gelatine; starch; cellulose polymers; casein; dextran and derivatives thereof; polysaccharides; fibrinogen; copolymers prepared from caprolactone and/or lactide and/or glycolide and/or polyethylene glycol, poly(valerolactone), polydioxanone and lactide; copolymers of lactide and 1,4-dioxane-2-one; poly(hydroxybutyrate); poly(hydroxyvalerate); poly(hydroxybutyrate-co-hydroxyvalerate) copolymers; poly(alkylcarbonate); poly(orthoesters); tyrosine based polycarbonates and polyarylates; poly(ethylene terephthalate); poly(anhydrides); poly(esteramides); polyphosphazenes; poly(amino acids); poly-L-lactic acid (PLLA); poly-D,L-lactic acid (PDLLA); polyglycolic acid (PGA); copolymers of polylactic acid; polyglycolic acid (PLGA); polycaprolactone; poly (4-hydroxybutyrate) (P4HB); polydioxanone; poly (trimethylene carbonate); poly (hydroxybutyrate-hydroxyvalerate); polyorthoester; poly(ester amides); poly (ortho esters); polyanhydrides; poly (anhydride-co-imide); poly (propylene fumarate); pseudo poly (amino acid); poly (alkyl cyanoacrylates); polyphosphazenes; and polyphosphoester.

Aspect 43. The tubing of Aspect 42 wherein the polymeric material is Poly (L-lactide), Poly (D,L-lactide), Poly(glycolide) or copolymers and/or blends thereof.

Aspect 44. The tubing of Aspect 43 wherein the polymeric material is Poly (L-lactide).

Aspect 45. The tubing of any one of Aspects 35 to 44 wherein the polymeric material has a crystallinity from 5 to 90%, preferably from 30 to 70%.

Aspect 46. A tube produced by the method of any one of Aspects 1 to 33.

Aspect 47. The tube according to Aspect 46, where in the tube is defined as in any one of Aspects 35 to 45.

Aspect 48. A stent formed from the tubing of any one of Aspects 35 to 47, optionally wherein the stent is a vascular stent, a ureteral stent, a urethral stent, a duodenal stent, a colonic stent or a biliary stent.

Aspect 49. The stent of Aspect 48 wherein the stent is a coronary stent or a peripheral, a cardiothoracic, or a neuro vascular stent, optionally wherein the stent is expandable.

Aspect 50. The stent of Aspect 48 or Aspect 49, wherein the stent undergoes a surface erosion process.

Aspect 51. The stent of any one of Aspects 48 to 50, wherein the inner diameter is between 0.5 to 4.5 mm when expanded for coronary stents or between 2.0 to 10.0 mm when expanded for peripheral stents.

Aspect 52. The stent of any one of Aspects 48 to 51, wherein the stent biodegrades over a period of 6 months to 36 months following implantation in an organism.

Aspect 53. The stent of any one of Aspects 48 to 52, capable of withstanding expansion pressures of between 5 and 20 bar.

Aspect 54. The stent of any one of Aspects 48 to 53 further comprising radioopaque markers.

Aspect 55. The stent of Aspect 54, wherein the radioopaque markers are selected from one or more of platinum, tantalum, tungsten, barium carbonate, bismuth oxide, barium sulfate, metrazimide, iopamidol, iohexol, iopromide, iobitridol, iomeprol, iopentol, ioversol, ioxilan, iodixanol, iotrolan, acetrizoic acid derivatives, diatrizoic acid derivatives, iodo-pyrimido-pyrimidne derivatives, iodo-theophylline derivatives iothalamic acid derivatives, ioxithalamic acid derivatives, metrizoic acid derivatives, iodamide, lypophylic agents, iodipamide and ioglycamic acid or, by the addition of microspheres or bubbles which present an acoustic interface.

Aspect 56. The stent of any one of Aspects 48 to 55 further comprising a biologically active agent.

Aspect 57. The stent of Aspect 56, wherein the biologically active agent is selected from one anti-proliferatives, anti-coagulants, vasodilators, anti-inflammatories cytotoxic agents, antibiotics and radioactive agents or targets thereof, for local radiation therapy.

Aspect 58. The stent of any one of Aspects 48 to 57, further comprising an acid scavenging agent, optionally wherein the acid scavenging agent is mopidamol or derivatives thereof.

The invention claimed is:

1. A method of producing a tube for use in the formation of a stent, said method comprising:
   deforming an orientable, thermoplastic polymer tubing in the solid phase by drawing it over a mandrel, where the mandrel has a lead end and an exit end, and through a die, where the die has an entry side and an exit side wherein:
   a drawing mechanism applies a drawing tension to the tubing from the exit end of the mandrel and the exit side of the die, said tension being insufficient to cause tensile failure of the tubing but sufficient to deform the tubing, thereby drawing the tubing over the mandrel and through the die in the solid phase to induce uniaxial or biaxial orientation of the polymer; and
   collecting the deformed tubing from the exit end of the mandrel and exit side of the die;
   wherein the orientable, thermoplastic polymer tubing has an inner diameter from 0.5 mm to 4.0 mm, and an outer diameter from 0.9 mm to 15 mm;
   the diameter of the mandrel at its widest point is from 0.01 to 15 mm;
   the wall thickness of the deformed tubing is from 75 to 300 microns; and
   wherein the die is a diverging die or a parallel die.

2. The method according to claim 1, wherein the orientable, thermoplastic polymer tubing is heated to a temperature above the glass transition temperature and below the melting temperature of the thermoplastic polymer.

3. The method according to claim 1, wherein the bulk cross-sectional area of the polymeric tubing is reduced by drawing said tubing over the mandrel.

4. The method according to claim 1, wherein the mandrel is an expanding cone mandrel.

5. The method according to claim 4, wherein the expanding cone mandrel has a taper with an angle of inclination of the taper from 5 to 60 degrees.

6. The method according to claim 1, wherein the entry side of the die has a diameter from 0.4 to 8.00 mm or the exit side of the die has a diameter from 1.0 to 15 mm or both.

7. The method according to claim 1, wherein the die has a semi angle of the die entry or a semi angle of the die exit or both semi angles of the die entry and of the die exit have the semi angle from 0 to 50 degrees.

8. The method according to claim 1, wherein the ratio of the die entry or exit angle and an angle of inclination of the mandrel taper is in the range of 1:1 to 10:1.

9. The method according to claim 1, wherein an inner hoop draw ratio is at least 1.5 or wherein an axial draw ratio is from 1.5:1 to 15:1 or both.

10. The method according to claim 1, wherein a ratio of an axial draw ratio to an inner hoop draw ratio is in the range of 0.5:1 to 10:1.

11. The method according to claim 1, further comprising the step of extruding the thermoplastic polymeric tubing from an upstream extruder prior to the deformation step.

12. The method according to claim 1, wherein a cooling of the orientable, thermoplastic polymer tubing starts while in contact with the die and/or mandrel or immediately after said tubing has been drawn over the mandrel and/or through the die.

13. The method according to claim 1, wherein the orientable, thermoplastic polymer tubing for use in said method has a wall thickness of 0.1 mm to 1.0 mm.

14. The method according to claim 1 further comprising preparing a stent from the deformed tubing.

15. The method according to claim 4, wherein the expanding cone mandrel has a taper with an angle of inclination of the taper from 20 to 40 degrees.

16. The method according to claim 1, wherein the entry side of the die has a diameter from 2.0 to 4.0 mm.

17. The method according to claim 1, wherein the die is a diverging die.

18. The method according to claim 1, wherein a semi angle of the die entry and/or die exit is from 20 to 40 degrees.

19. The method according to claim 1, wherein a ratio of the die entry or exit angle and an angle of inclination of a mandrel taper is in the range of 1:1 to 5:1.

20. The method according to claim 1, wherein an axial draw ratio is from 2.5:1 and 4:1.

21. The method according to claim 1, wherein the wall thickness of the deformed tubing is from 75 to 150 microns.

* * * * *